(12) United States Patent
Alexander et al.

(10) Patent No.: US 9,861,800 B2
(45) Date of Patent: Jan. 9, 2018

(54) SYSTEMS AND METHODS FOR CONTROLLING BALLOON CATHETERS

(71) Applicants: Ian Joseph Alexander, Los Alamos, NM (US); Brian Dean Owens, Plano, TX (US)

(72) Inventors: Ian Joseph Alexander, Los Alamos, NM (US); Brian Dean Owens, Plano, TX (US)

(73) Assignee: TREBLE INNOVATIONS, Springville, UT (US)

( * ) Notice: Subject to any disclaimer, the term of this patent is extended or adjusted under 35 U.S.C. 154(b) by 7 days.

(21) Appl. No.: 13/654,401

(22) Filed: Oct. 17, 2012

(65) Prior Publication Data

US 2013/0096378 A1    Apr. 18, 2013

Related U.S. Application Data

(60) Provisional application No. 61/548,596, filed on Oct. 18, 2011, provisional application No. 61/559,190, filed on Nov. 14, 2011, provisional application No. 61/585,658, filed on Jan. 12, 2012, provisional application No. 61/595,885, filed on Feb. 7, 2012.

(51) Int. Cl.
*A61B 1/00* (2006.01)
*A61M 25/06* (2006.01)
(Continued)

(52) U.S. Cl.
CPC ......... *A61M 29/00* (2013.01); *A61B 1/0002* (2013.01); *A61B 1/005* (2013.01); *A61B 1/0014* (2013.01); *A61B 1/00016* (2013.01); *A61B 1/00018* (2013.01); *A61B 1/00101* (2013.01); *A61B 1/00108* (2013.01); *A61B 1/00114* (2013.01); *A61B 1/00135* (2013.01); *A61B 1/00142* (2013.01); *A61B 1/00154* (2013.01); *A61B 1/05* (2013.01); *A61B 1/0676* (2013.01); *A61B 1/233* (2013.01); *A61M 25/0662* (2013.01); *A61M 25/10* (2013.01); *A61M 25/1018* (2013.01); *A61M 25/1025* (2013.01); *A61M 29/02* (2013.01); *A61B 1/00032* (2013.01);
(Continued)

(58) Field of Classification Search
CPC ............ A61B 1/00133; A61B 1/00135; A61B 1/0125; A61B 1/00142; A61B 1/00154; A61M 25/0662; A61M 25/10; A61M 25/1018; A61M 25/1025; A61M 2025/1043; A61M 29/00; A61M 29/02
USPC ....... 600/104, 118, 141, 146, 152, 153, 114, 600/121–125, 115
See application file for complete search history.

(56) References Cited

U.S. PATENT DOCUMENTS 4,862,874 A * 9/1989 Kellner .................. 600/116
5,025,778 A * 6/1991 Silverstein ........... A61B 1/0008
600/104
(Continued)

FOREIGN PATENT DOCUMENTS

JP          2005046273 A  *  2/2005

*Primary Examiner* — Timothy J Neal
*Assistant Examiner* — Aaron B Fairchild
(74) *Attorney, Agent, or Firm* — Goodhue, Coleman & Owens, P.C.

(57) ABSTRACT

A system and method for utilizing an endoscopic sheath. An endoscope is received in a scope port of the endoscopic sheath. A dilation device is received in a working port of the endoscopic sheath. The dilation device is controlled utilizing controls of the endoscopic sheath.

8 Claims, 14 Drawing Sheets

(51) Int. Cl.
*A61M 25/10* (2013.01)
*A61M 29/02* (2006.01)
*A61M 29/00* (2006.01)
*A61B 1/005* (2006.01)
*A61B 1/05* (2006.01)
*A61B 1/06* (2006.01)
*A61B 1/233* (2006.01)
*A61B 1/04* (2006.01)

(52) U.S. Cl.
CPC ......... *A61B 1/0051* (2013.01); *A61B 1/00052* (2013.01); *A61B 1/00066* (2013.01); *A61B 1/00133* (2013.01); *A61B 1/04* (2013.01); *A61M 2025/1043* (2013.01)

(56) References Cited

U.S. PATENT DOCUMENTS

| | | | |
|---|---|---|---|
| 5,257,617 A * | 11/1993 | Takahashi | A61B 1/00142 600/123 |
| 5,318,008 A * | 6/1994 | Bullard | A61B 1/0056 600/139 |
| 5,599,301 A * | 2/1997 | Jacobs et al. | 604/65 |
| 6,165,123 A * | 12/2000 | Thompson | A61B 1/00142 600/114 |
| 2002/0068851 A1* | 6/2002 | Gravenstein | A61B 1/2676 600/121 |
| 2003/0130564 A1* | 7/2003 | Martone | A61B 1/00071 600/121 |
| 2005/0075538 A1* | 4/2005 | Banik | A61B 1/00071 600/141 |
| 2005/0228224 A1* | 10/2005 | Okada | A61B 1/00071 600/104 |
| 2006/0161045 A1* | 7/2006 | Merril et al. | 600/117 |
| 2006/0235458 A1* | 10/2006 | Belson | A61M 25/0032 606/191 |
| 2007/0185377 A1* | 8/2007 | Murakami | A61B 1/00059 600/106 |
| 2009/0076330 A1* | 3/2009 | Ashida | 600/146 |
| 2010/0063358 A1* | 3/2010 | Kessler | 600/121 |

* cited by examiner

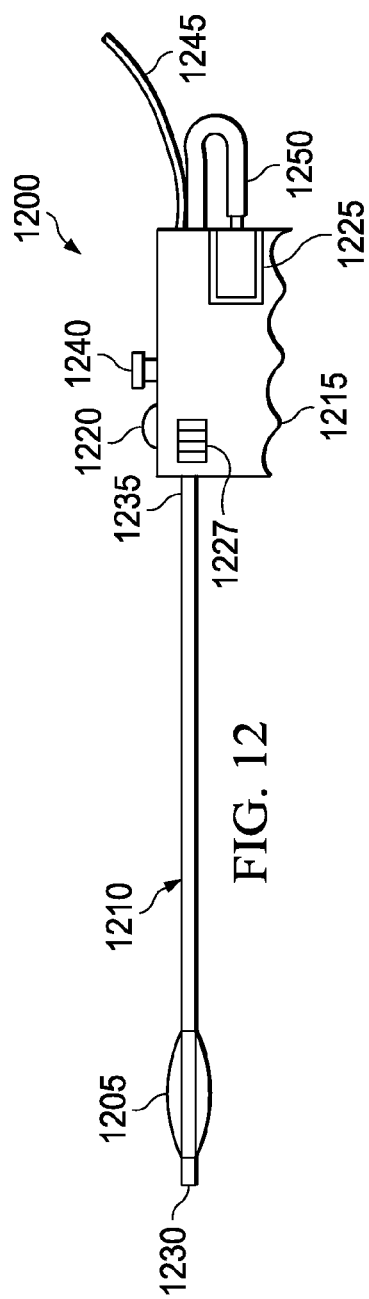
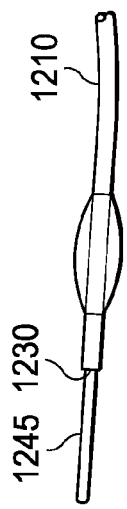
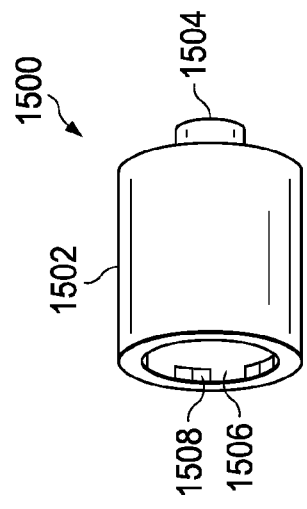
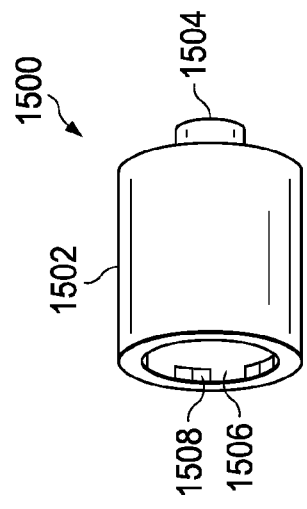

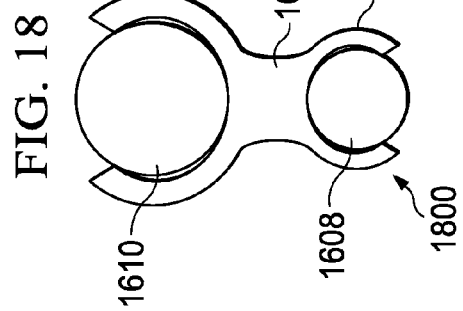
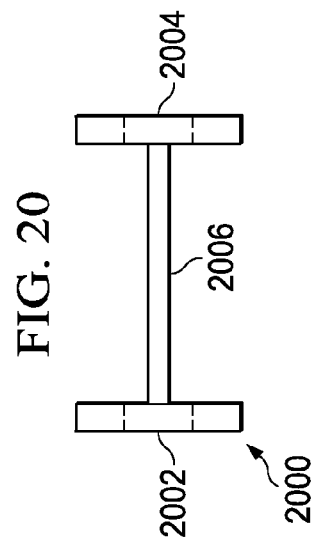
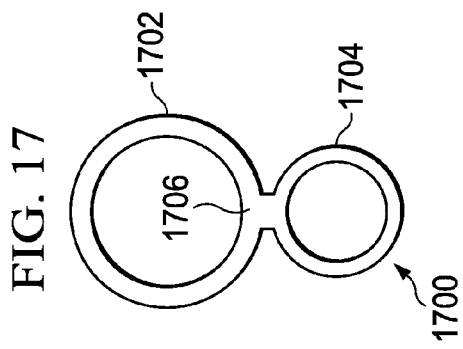
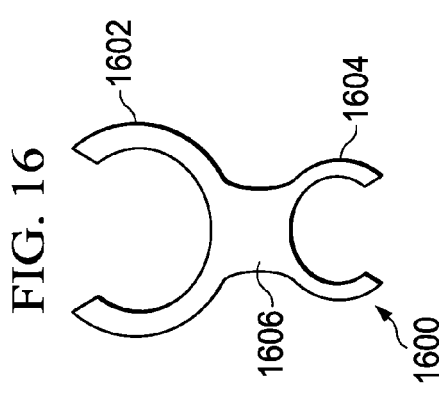
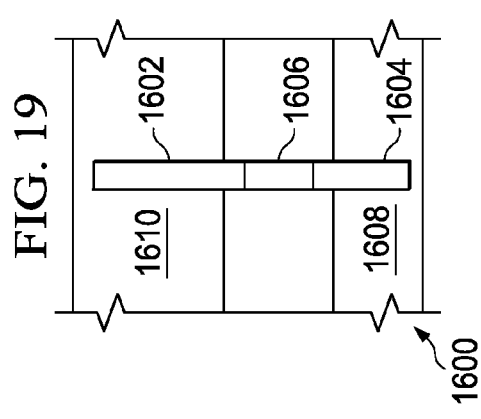

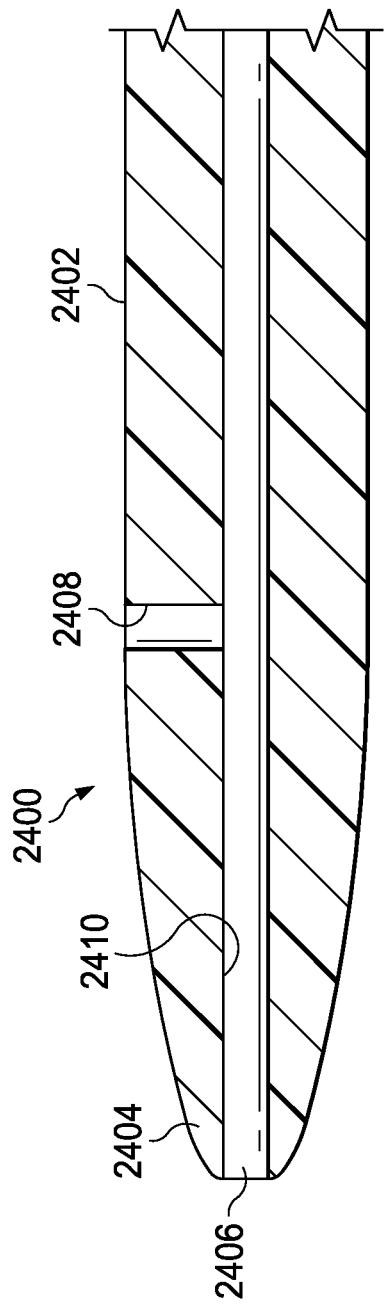
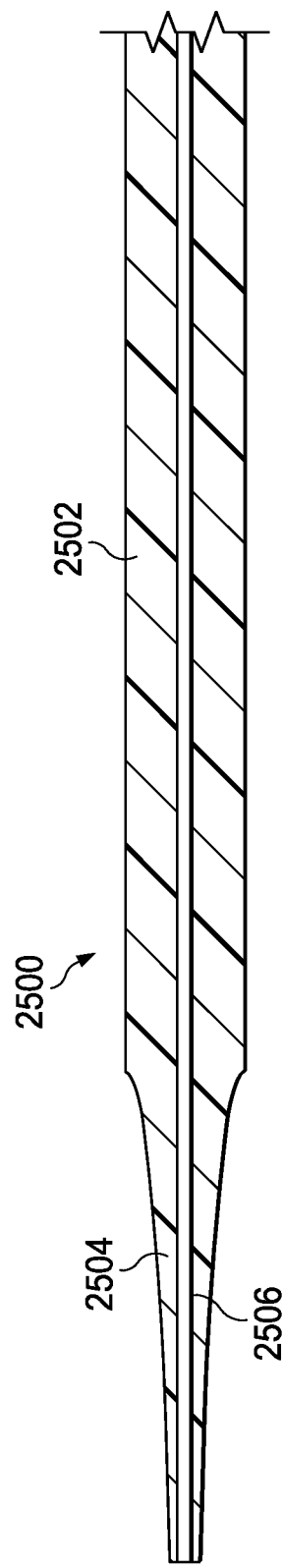

SYSTEMS AND METHODS FOR CONTROLLING BALLOON CATHETERS

RELATED APPLICATIONS

This Application claims priority to U.S. provisional patent application Ser. No. 61/548,596 entitled "Nasal Guide and Method of Use Thereof", filed Oct. 18, 2011, U.S. provisional patent application Ser. No. 61/559,190 entitled "Portable Endoscope and Method of Use Thereof", filed Nov. 14, 2011, U.S. provisional patent application Ser. No. 61/585,658 entitled "Endoscopic Sheath and Method of Use Thereof", filed Jan. 12, 2012, and U.S. provisional patent application Ser. No. 61/595,885 entitled "Systems and Methods for Controlling Balloon Catheters" filed Feb. 7, 2012 the entire contents of which are all hereby incorporated by reference in their entirety. This Application is related to U.S. utility patent application Ser. No. 13/654,409 entitled "Endoscopic Peripheral", filed Oct. 17, 2012, the entire contents of which are all hereby incorporated by reference in their entirety.

BACKGROUND

Each year more and more surgical procedures are performed endoscopically. Endoscopy refers to looking inside the body for medical reasons using an endoscope. An endoscope is an instrument utilized to examine the interior of the body through an orifice or a naturally or surgically created opening. The endoscope is typically inserted directly into the applicable organ or body part.

For example, balloon sinuplasty, brain surgery, enteroscopy, rhinoscopy, esophagogastroduodenoscopy, and cosmetic surgery may be performed endoscopically through the nose or other orifice (natural or surgically created) of a patient out of necessity or convenience. In particular, balloon sinuplasty has become more popular in recent years because of enhanced equipment and minimal down time for the patient. Balloon sinuplasty is an endoscopic surgical procedure for the treatment of conditions, such as blocked nasal sinuses. Because the procedure involves the insertion into the nose of balloon catheters, guide wires, and other devices and instruments, such as irrigation catheters, illumination systems, and navigation systems, individuals might become uncomfortable and find it difficult to remain still. For example, a physician may insert the sinus guide catheter into a nostril of a patient to gain access to the sinus ostia under endoscopic visualization.

Properly performing endoscopic procedures and surgeries in the body of the patient require correct positioning of the necessary instrumentation, devices, and equipment. Some procedures may require multiple medical professionals to ensure proper guidance and placement of the equipment due the size and awkwardness of the equipment. In addition, the costs for most medical equipment utilized to perform endoscopic medical procedures are very high. In part, the costs are high due to the FDA approval process, manufacturing, and packing limitations and expenses associated with those processes.

SUMMARY

One embodiment provides a system and method for utilizing an endoscopic sheath. An endoscope is received in a scope port of the endoscopic sheath. A dilation device is received in a working port of the endoscopic sheath. The dilation device is controlled utilizing controls of the endoscopic sheath.

Another embodiment provides an endoscopic sheath. The endoscopic sheath may include a scope port configured to receive an endoscope. The endoscopic sheath may further include a working port configured to receive a medical instrument.

Yet another embodiment provides a method of utilizing an endoscopic sheath. A wireless endoscope may be received entirely within a scope port of the endoscopic sheath. A medical instrument may be received in a working port of the endoscopic sheath. The medical instrument may be controlled utilizing controls of the endoscopic sheath including at least inserting and retracting the medical instrument.

BRIEF DESCRIPTION OF THE DRAWINGS

Illustrative embodiments of the present invention are described in detail below with reference to the attached drawing figures, which are incorporated by reference herein and wherein:

FIG. 12 is a schematic, plan view of a sheath balloon system in accordance with an illustrative embodiment;

FIG. 13 is a schematic, plan view of a portion of the balloon sheath system of FIG. 12 including the first end in accordance with an illustrative embodiment;

FIGS. 14-15 are schematic, perspective views of inflation cartridges in accordance with illustrative embodiments;

FIG. 16 is a schematic, plan view of a connector in accordance with an illustrative embodiment;

FIG. 17 is a schematic, plan view of a connector in accordance with another illustrative embodiment;

FIG. 18 is a schematic, plan view of a connector securing a balloon catheter system and a portable endoscope in accordance with an illustrative embodiment;

FIG. 19 is a schematic, side view of the connector of FIG. 16 in accordance with an illustrative embodiment;

FIG. 20 is a schematic, side view of a connector in accordance with an illustrative embodiment;

FIG. 24 is a schematic, cut-away view of a video bougie in accordance with an illustrative embodiment;

FIG. 25 is a schematic, cut-away view of a video bougie in accordance with another illustrative embodiment;

DETAILED DESCRIPTION OF THE DRAWINGS

The illustrative embodiments provide a system, method, and endoscopic sheath for performing endoscopic procedures. The endoscopic sheath may also be referred to genetically as a sheath. In one embodiment, the sheath is a receptacle utilized to cover an endoscope or borescope (hereinafter "endoscope" or "scope") without limiting the features of the endoscope. The illustrative embodiments may be utilized with borescopes that are not FDA approved because the borescope does not come into contact with the patient (only the endoscopic sheath does). As a result, costs associated with endoscopes may be decreased significantly. The endoscopic sheath may be sterile and suited for use within a body of a patient.

In one embodiment, a portable or wireless endoscope may be entirely or partially inserted into a scope port of the endoscopic sheath, in another embodiment, the endoscopic sheath may be configured to receive an endoscope (e.g., fiber optic endoscope, fixed endoscope, etc.), balloon device or catheter, or other medical instrument, such as those manufactured by Acclarent, Entellus, Entrigue, and other parties. The endoscopic sheath also provides an enhanced grip for maneuvering the endoscope. The endoscopic sheath may be disposable and suited for a one-time-use or may be cleaned and sanitized for repeated usage. The size and configuration of the endoscopic sheath may vary based on the medical procedure being performed.

The illustrative embodiments may also provide an inflation cartridge, a connector, a video bougie, a portable endoscope, and an inflation handle, that may be utilized to perform medical procedures. For example, the described systems and methods may be utilized to perform nasal dilation. The illustrative embodiments also provide improved features, controls, components and devices for existing medical instruments. Unless otherwise indicated, as used herein, "or" does not require mutual exclusivity. Content captured by the described image capture and camera systems include still images, video of various spectra and may be referred to interchangeably as "video", "image content", or so forth.

Figure 1:
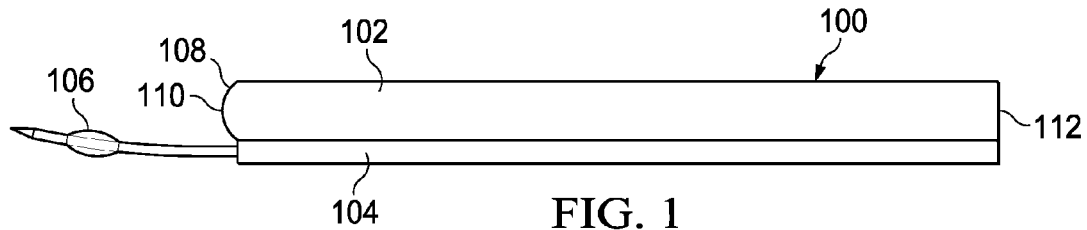
FIG. 1 is a schematic, plan view of an endoscopic sheath in accordance with an illustrative embodiment.

Turning now to FIG. 1, a schematic, plan view of an endoscopic sheath 100 is shown in accordance with an illustrative embodiment. Depending on the medical application, FIG. 1 may be a complete or partial view of the endoscopic sheath 100. The endoscopic sheath 100 may include any number of components. In one embodiment, the endoscopic sheath 100 includes a scope port 102, a working port 104, a balloon catheter 106, a lens 108, a first end 110 and a second end 112.

The scope port 102 may be a closed-ended port for receiving an endoscope (not shown). In one embodiment, the scope port 102 is open at the second end 112 and closed at the first end 110. In another embodiment, both the first end 110 and second end 112 may be open. The second end 112 may be flared for more easily receiving instruments. In one embodiment, the first end 110 is transparent or acts as a lens for a light or camera of the endoscope. The lens 108 may be configured to enhance the images captured by the endoscope and may be attached to the first end 110 utilizing threads, friction based on tolerances (snaps to the scope port 102), tabs, an interference fit, or other securing components or techniques.

Exterior walls and interior walls of the endoscopic sheath 100 may be smooth for easy insertion of the endoscopic sheath 100 into a body of the patient and for receiving the endoscope, respectively. The endoscopic sheath 100 may be any length corresponding to the medical procedure and a length of the endoscope. For example, the endoscopic sheath 100 may be particularly useful for performing balloon sinuplasty and may only be six inches long. Similarly, the diameter and shape of the scope port 102 and the working port 104 may vary based on the particular medical application (e.g., circular, oval, square, etc). For example, the endoscopic sheath 100 may be much longer or wider when utilized for gastrointestinal or examinations of large animals, such as cows and horses.

The working port 104 may have open ends at the first end 110 and the second end 112. As a result, the balloon catheter 106 may be passed through the working port 104. The balloon catheter 106 is one example of a medical instrument or instruments that may be utilized to perform a medical procedure, such as balloon sinuplasty. Lights, cameras, lasers, clamps, surgical tools, and irrigation and suction components, are other examples that may be pushed through the working port 104 alone or in combination with another component. For example, the balloon catheter 106 may include a guide wire, catheter, and a balloon as is known in the art. The balloon catheter 106 may be inserted into a sinus of the patient and then inflated to forcibly expand portions of the sinus for any number of medical reasons. The balloon catheter 106 may be controlled, guided, or inflated by medical instruments (not shown) that may connect to or extend from the second end 112 of the endoscopic sheath 100.

In another embodiment, the scope port 102 and the working port 104 may include guides, rails, ridges, or other securing structures for connecting or receiving additional medical instruments (e.g. a thin fiber optic light). The endoscopic sheath 100 may be configured to actively or passively attach to an endoscope.

Figure 2:
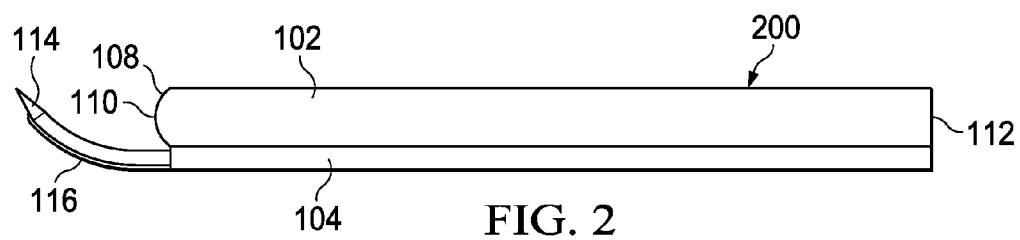
FIG. 2 is a schematic, plan view of another endoscopic sheath in accordance with an illustrative embodiment.

Turning now to FIG. 2, an illustrative embodiment of the endoscopic sheath 200 is shown. In this embodiment, the endoscopic sheath 200 may include a curved guide 116. The curved guide 116 is an extension from the second end 112 of the endoscopic sheath 200. The curved guide 116 may be utilized to redirect or guide components that are passed through the working port 104. The curved guide 116 may be pre-configured (bendable by hand or once heated) or selected (from a plurality of angles and lengths) for reaching a sinus or other body part. The curved guide 116 may be integrated with or externally attached to the endoscopic sheath 200. For example, the curved guide 116 may snap into a port of the endoscopic sheath 200 below or part of the working port 104.

In one embodiment, a bougie 114 is communicated through the working port 104. The curved guide 116 redirects the bougie 114 upward as shown in FIG. 2. The curved guide 116 may utilize any number angles or directions applicable to the medical procedure being performed. As shown, the bougie 114 is redirected from the straight path out of the working port 104. For example, by utilizing the curved guide 116 a medical professional may more easily insert the bougie 114 into a particular sinus of the patient.

The bougie 114 may include a conical tip for dilating or opening the sinuses of the patient. The bougie 114 may be self-guided or controlled by the guiding components of the endoscopic sheath 100 as are subsequently described. The shape utilized at the end of the bougie 114 may vary based on the application and the sensitivity of tissues, organs, membranes, and other body parts involved as is subsequently described.

Figure 3:
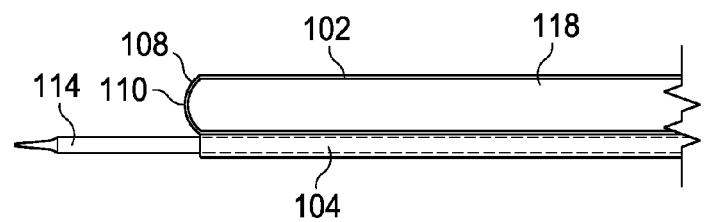
FIG. 3 is a schematic, plan view of a portion of an endoscopic sheath in accordance with an illustrative embodiment.

FIG. 3 further illustrates an endoscope 118 being inserted into the scope port 102 and the bougie 114 passing through die working port 104. As is shown, the endoscope 118 and the scope port 102 may share a similar or complementary shape (e.g. diameter, cross sectional shape, etc). In one embodiment, the proximity of the endoscope 118 and the scope port 102 at the first end 110 may prevent distortion of the image and video signals generated by the endoscope 118. The first end 110 may further include the lens 108 or a transparent cover facilitating visualization by the endoscope 118 through the first end 110 of the endoscope 118.

Figure 4:
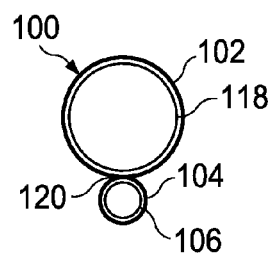
FIGS. 4 and 5 are front views of embodiments of the endoscopic sheath of FIG. 1 in accordance with illustrative embodiments.
Figure 5:
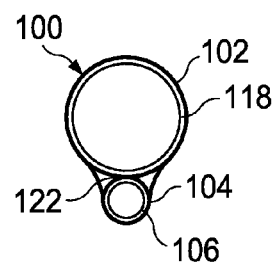

FIGS. 4 and 5 show embodiments of the front view of the endoscopic sheath 100. In FIG. 4, the scope port 102 is connected, fused, or otherwise coupled directly to the working port 104. The endoscope 118 may be inserted within the scope port 102 and the balloon catheter 106 may be inserted in the working port 104. The scope port 102 and the working port 104 are preferably sized such that an endoscope 118 and the balloon catheter 106, respectively, may be inserted and removed without requiring excessive force. As shown in FIG. 4, the scope port 102 and the working port 104 may be positioned in a figure eight configuration, in one embodiment, the combined diameters (or vertical length) of both the scope port 102 and the working port 104 are less than 0.75 cm. However, the diameters may vary based on the application and examination location.

FIG. 5 shows another embodiments that differs in that supports 122 attach or support the scope port 102 and the working port 104. The supports 122 may be solid plastic or a framework that fuses or integrates the scope port 12 and the working port 104. The supports 122 may be desirable during medical procedures in which additional forces are applied to the endoscopic sheath 100. In one embodiment, the scope port 102, the working port 104, and/or the supports 122 may be hinged, bend, or be flexible for pointing the end of the endoscopic sheath 100 in a particular direction (see FIG. 6). The endoscopic sheath 100 may also be configured to be extremely flexible for extensive insertion into sensitive body parts or organs.

Figure 6:
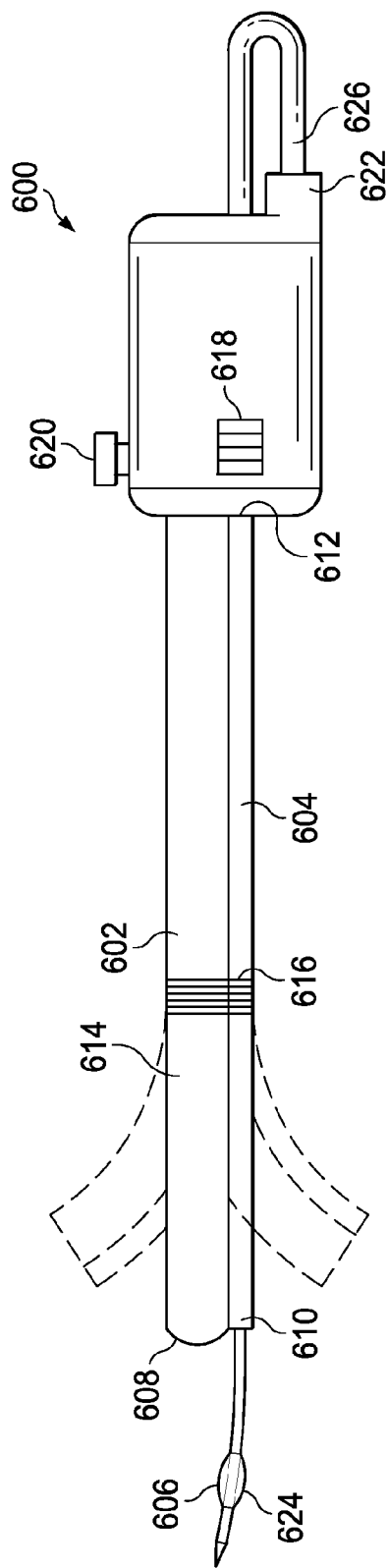
FIG. 6 is a schematic, plan view of an endoscopic sheath in accordance with another illustrative embodiment.
Figure 26:
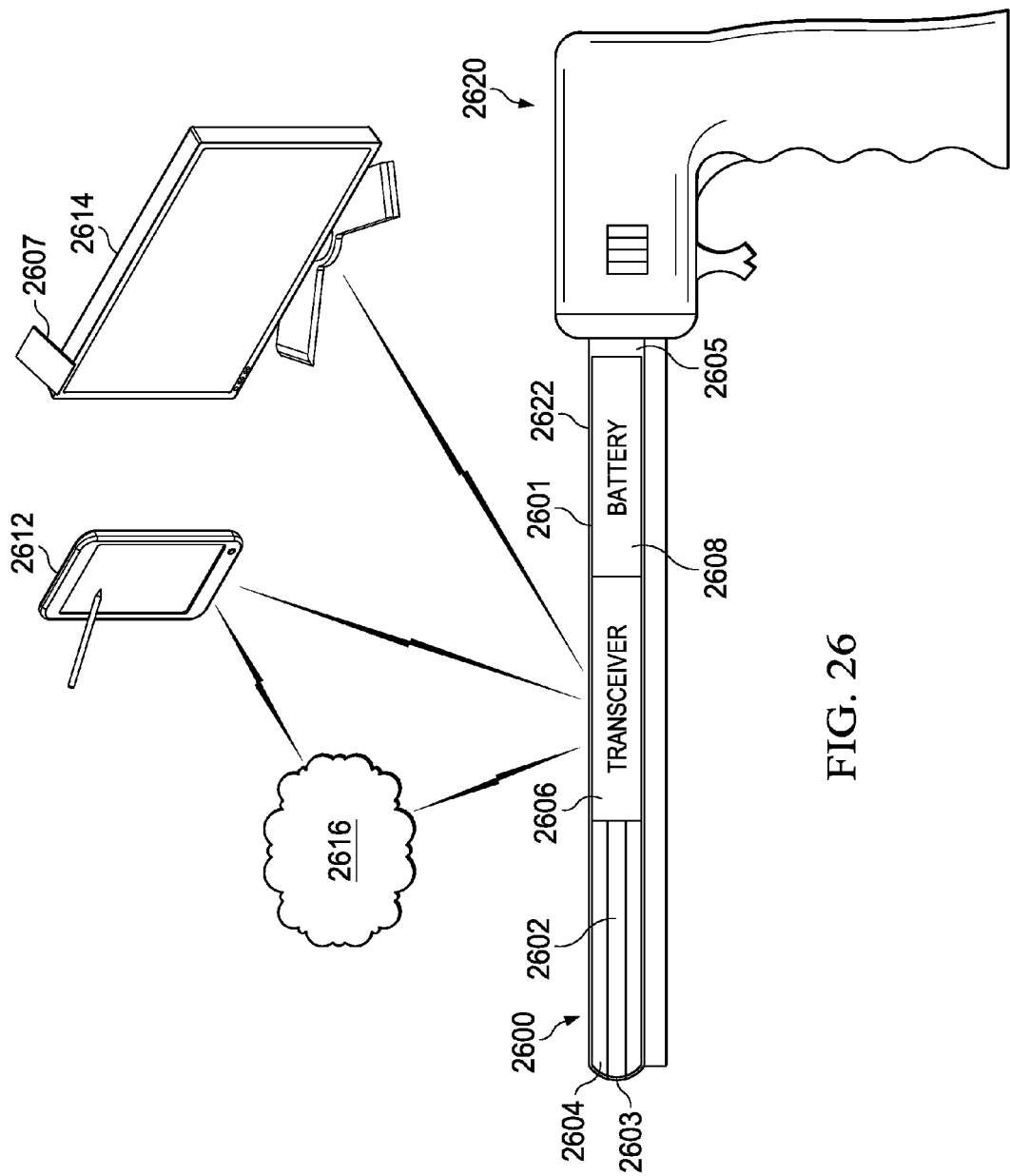
FIG. 26 is a schematic, pictorial representation of a portable endoscope and an endoscopic sheath is shown in accordance with an illustrative embodiment.

The embodiments of endoscopic sheaths as are shown in FIGS. 6-10 may be configured to receive a portable endoscope as described in FIG. 26 or a hard-wired endoscope as is known in the art. FIG. 6 is a schematic, plan view of an endoscopic sheath 600 in accordance with another illustrative embodiment. In one embodiment, the endoscopic sheath 600 may include a scope port 602, a working port 604, a balloon catheter 606, a lens 608, a first end 610, a second end 612, a bending section 614, a hinge 616, an advancer 618, a directional control 620, and an inflation port 622.

In one embodiment, the bending section 614 is configured to flex, bend, or curve vertically or approximately along a single plane. As a result, the first end 610 of the endoscopic sheath 600 may be focused at a particular portion of the body, such as a sinus. The directional control 620 may be utilized to control the bending section 614 of the endoscopic sheath 600. For example, the medical professional may move the directional control 620 with a band to move the bending section 614 in a downward direction. Similarly, the medical professional may pull back on the directional control 620 to move the bending section 614 upward. In another embodiment, the bending section 614 may move in both a horizontal and vertical direction, or along two orthogonal or non-orthogonal planes of motion. The directional control 620 may similarly be moved in two dimensions to control the horizontal (x axis) and vertical movement (y axis) of the bending section 614.

The directional control 620 and the bending section 614 may be mechanically or electronically linked to achieve the desired motion, in one embodiment, cables (not shown) may be mechanically connected to the bending section 614 and may be controlled by the directional control 620 to move the bending section 614. The cables may run within their own sleeves, guides, or ports, internal or external to the scope port 602 and the working port 604, to attach to both ends. For example, die directional control 620 may be a toggle that mechanically or electrically moves the bending section 614.

In another embodiment, the bending section 614 may include one or more servos, electric motors, piezo electric devices, or other components for moving the bending section 614. The directional control 620 may control the movement through control signals sent through wires to the electronics of the bending section 614. One or more switches or digital logic components may generate die control signals for die bending section 614 in response to motion of die directional control 620.

In one embodiment, the bending section 614 bends about die hinge 616. For example, the hinge may be a corrugated or z-shaped portion of the scope port 602 and the working port 604 as is known in the art. In another embodiment, the entire portion of the bending section 614 may bend to reach a desired angle or position. The bending section 614 may also be moldable, set, or fixed to a particular position.

The scope port 602 may be configured to receive a rigid or flexible endoscope, portable endoscope, or borescope. For example, a less expensive borescope may be utilized in the endoscopic sheath 600 reducing the price of the system required to perform medical procedures or analysis. In addition, only the endoscopic sheath 600 may be required to meet FDA approval because die exterior of the endoscopic sheath 600 is die only instrument to touch or interact with the body of the patient. In addition, the motion of the endoscopic sheath 600 may be controlled by the endoscope or equivalent device inserted within the scope port 602.

The balloon catheter 606 may be flexible allowing an inflating end 624 to be connected to the inflation port 622. In one embodiment, the balloon catheter 606 is pre-charged with a liquid, such as saline. The inflating end 624 of the balloon catheter 606 may be sealed with foil or plastic that is ruptured or broken when inserted into the inflation port 622. In another embodiment, the balloon catheter 606 may include a removable seal (not shown). The balloon catheter 606 may then be pressurized with a liquid or gas to inflate the balloon. In one embodiment, the lumen(s) of the balloon catheter 606 may include ridged, collared, or narrowing sections near the inflating end 624, such that when air or gas is used to pressurize the balloon catheter 606, the air or associated bubbles are prevented from being communicated to the balloon end of the balloon catheter 606 to ensure compliant and uniform expansion of the balloon even when pressurized at a remote end 626 with air.

All or a portion of the balloon catheter 606 may also include ridges, indentations, notches steps, or other similar structures along the length of the balloon catheter 606 that allow the balloon catheter 606 to be advanced by a ratchet, pawl, guide wheels, arms, gears, or other component. In one embodiment, the indentations may be triangularly shaped indentations on one side, two sides, or around the entire diameter of the balloon catheter 606. In another embodiment, a portion of the balloon catheter 606 may have a square or triangular cross-section for manipulating and moving the balloon catheter 606. In one embodiment, the inflation port 622 may include a point for breaking a seal enclosing the remote end 626 of the balloon catheter 606 to enclose a pre-charged fluid. The body or handle of the endoscopic sheath 600 may include a miniature electric pump and battery (not shown) for powering the electric pump. The electric pump may pump liquid or a gas into the balloon catheter 606 to inflate the balloon portion of the balloon catheter 606.

The balloon catheter 606 may be of a pre-determined length for easy use with the endoscopic sheath 600. For example, the balloon catheter 606 may come pre-packaged and charged with saline. For nasal applications, the balloon catheter 606 may be pre-charged with saline and may be 12 cm long, in one non-limiting example. In one embodiment, the inflating or insertion end 624 of the balloon catheter 606 may be configured to release fluid in response to reaching an increased or threshold pressure (beyond the inflation pressure for the balloon). For example, the insertion end may include a thinner wall or port configured to break open or divide at a specified pressure, such as 25 atmospheres, to irrigate tissue or cavities. The release of fluids at the increased pressure may also be a safety mechanism to prevent a more explosive release of pressure that might injure a patient.

In one embodiment, the balloon catheter 606 may be inflated through the inflation port 622 in response to pushing perpendicular to the surface of the directional control 620 (rather than the parallel motion used to guide the scope port 602 and the working port 604). The balloon catheter 606 may deflate the balloon catheter or release the pressure in response to the medical professional removing the inflation pressure from the directional control 620. In one embodiment, the pump of the endoscopic sheath 600 may be configured to inflate the balloon catheter 606 to a pre-established pressure (e.g. 8-12 atmospheres) for a designated time period (e.g. 5-30 seconds) before automatically reducing the pressure.

The endoscopic sheath 600 may include one or more sensors indicating the pressure applied to the balloon catheter 606. In addition, the endoscopic sheath 600 may include any number of user interfaces, such as displays, vibrators, or speakers for indicating when the balloon catheter 606 has reached the pre-established pressure for the designated time period, if an excessive physical pressure is being applied against the end of the balloon catheter 606 (e.g. balloon catheter is caught on a tissue wall), or if a battery of the endoscopic sheath 600 is low. The endoscopic sheath 600 may utilize all mechanical controls and components, all electrical controls and components, or a combination thereof. In another embodiment, the endoscopic sheath 600 may include a dedicated button or other control for inflating the balloon catheter 606. Similarly, the advancer 618 may be utilized to inflate or deflate the balloon catheter 606 or provide irrigation.

In another embodiment, the endoscopic sheath 600 may be configured to receive a handle that extends or protrudes substantially or approximately perpendicularly from the body of die endoscopic sheath 600 and that may be utilized by the medical professional (or user) to more easily manipulate the endoscopic sheath 600.

Figure 7:
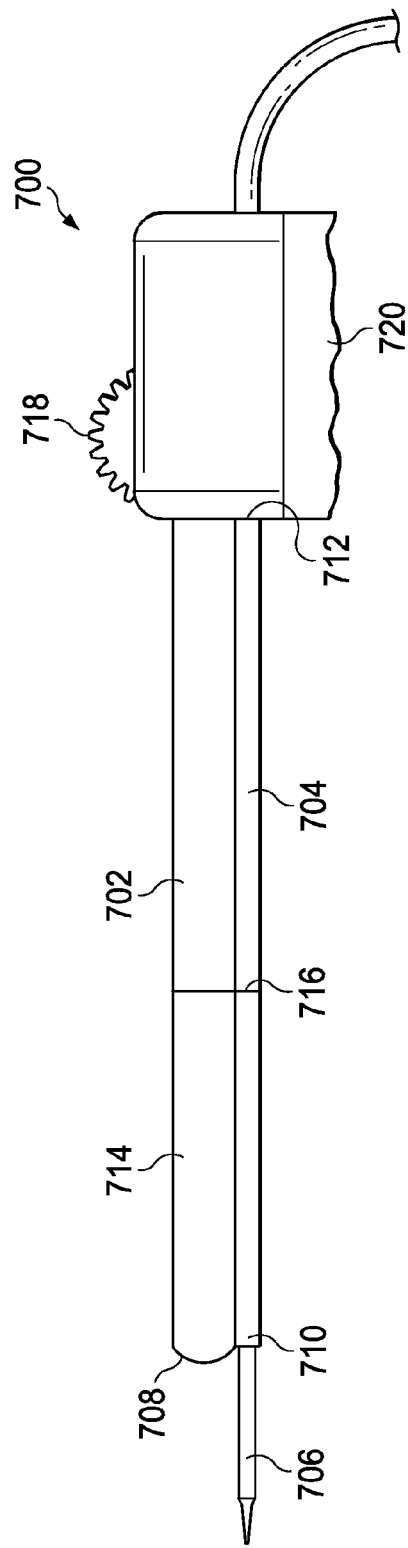
FIG. 7 is a schematic, plan view of an endoscopic sheath in accordance with another illustrative embodiment.

FIG. 7 is a schematic, plan view of an endoscopic sheath 700 in accordance with another illustrative embodiment. In one embodiment, the endoscopic sheath 700 may include a scope port 702, a working port 704, a bougie 706, a lens 708, a first end 710, a second end 712, a bending section 714, a hinge 716, an advancer 718, and a grip 720.

The endoscopic sheath 700 may be utilized to advance a bougie 706. The advancer 718 may be a control wheel that inserts and retracts the bougie 706 from the end of the working port 704. In one embodiment, the internal portion of the advancer 718 may include rollers, bearings, or clamps that both grip and move the bougie 706. In another embodiment, the bougie 706 (or inserted instrument) may be ribbed or have indentations along a portion of the bougie (e.g., a portion that does not enter the patient) for driving the bougie 706 utilizing a ratchet and pawl configuration. In one embodiment, the advancer 718 may allow the medical professional to feel the pressure exerted on die end of the bougie by tissue, blockages, or cavities. The advancer 718 may also be configured to slip in response to a pre-defined amount of pressure being asserted against the bougie. This may ensure that medical professional may sense the pressure being applied against the bougie 706 and may prevent the tissue, organs, cavities, or other body parts form being injured due to excessive force exerted by the bougie 706.

The bougie 706 may also be prepackaged and ready for insertion into the working port 704 of the endoscopic sheath 700. For example, the bougie 706 may be sterilized and ready to be threaded into the working port 704 and moved forward to the end of the working port by the advancer 718.

The endoscopic sheath 700 may include the grip 720 for allowing the medical professional to better hold the endoscopic sheath 700 during a procedure. In another embodiment, the grip 720 may include a hinge that allows the grip 720 to be turned from the horizontal position shown to a vertical position (or any position therebetween). The grip 720 may also include a locking mechanism (not shown) that allows the medical professional to fix the position of the grip 720. As a result, the medical professional may hold the endoscopic sheath 700 in whichever configuration is most convenient.

Figure 8:
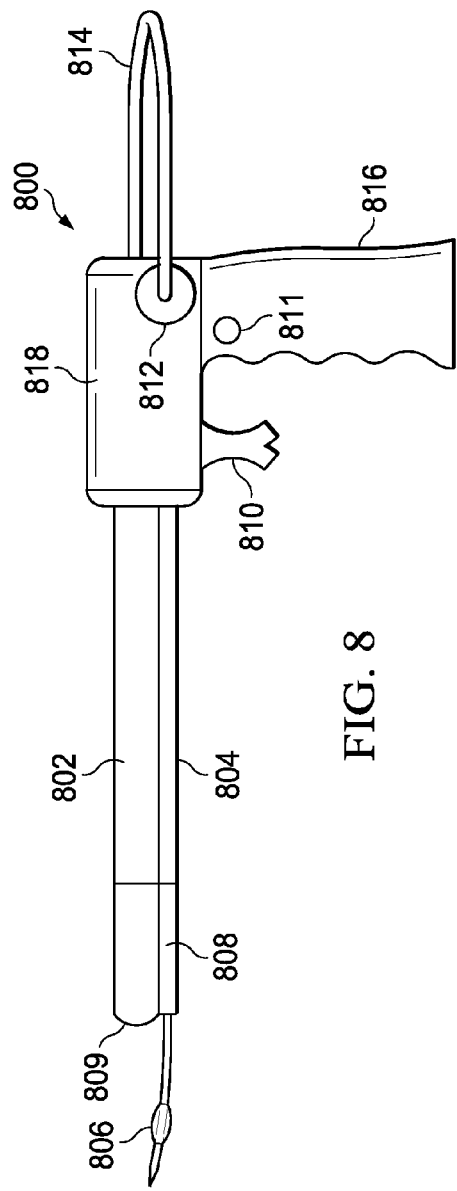
FIG. 8 is a schematic, plan view of another endoscopic sheath 800 in accordance with an illustrative embodiment.

FIG. 8 is a schematic, plan view of another endoscopic sheath 800 in accordance with an illustrative embodiment. In addition to previously disclosed components, the endoscopic sheath 800 may include a scope port 802, a working port 804, a balloon catheter 806, a bending section 808, a first end 809, an advancer 810, an inflation control 811, an inflation port 812, a second end 814 of the balloon catheter 806, and a handle 816.

In the endoscopic sheath 800, the balloon catheter 806 is advanced by the medical professional selecting the advancer 810. In one embodiment, the handle 816 is a pistol type grip and the advancer 810 is a trigger or two-way trigger for advancing and retracting the balloon catheter 806. For example, the medical professional may grip the handle 816 using a right or left hand. The advancer 810 may be operated utilizing and front and rear surface of the operator's index finger. Pulling the advancer 810 toward the handle 816 may proportionately advance the balloon catheter 806.

In one embodiment, a clamp, linkage, or rollers attached to the advancer 810 (not shown) may mechanically move the balloon catheter 806. However, any number of advancing systems may be used, such as a spring loaded metal plate that locks the balloon catheter 806 whenever the medical professional deselects the advancer 810 (allowing for finite advancement and retraction of the balloon catheter 806). For example, as the medical professional pulls the advancer 810, the lock plate may be released slightly to allow the balloon catheter 806 to move. Once the advancer 810 is released, the balloon catheter 806 may be locked in place by the spring loaded bar. In another embodiment, a portion of the balloon catheter 806 may include grooves, indentations, or steps allowing a ratcheting mechanism to advance and retract the balloon catheter 806. The advancer 810 may provide feedback to the medical professional indicating the pressure being applied to the tip of the balloon catheter 806 or other portion of the balloon.

In another embodiment, the advancer 806 may electronically control a small motor (not shown) for slowly and smoothly advancing and retracting the balloon catheter 806. The mechanical and electrical embodiments may be configured to slip if pressure beyond a threshold is applied to the balloon catheter 806 to prevent injuries to the patient. For example, the medical professional desires to not tear or puncture some of the soft tissues, skin, cartilage, membranes, and walls within the nasal cavities and sinuses and if excessive pressure is applied, the medical professional may inadvertently harm the patient. For example, the endoscopic sheath 800 may include a dial for increasing or decreasing the maximum pressure that may be physically applied to the balloon catheter 806 before it begins to slip or stop altogether. The inflation pressure may be similarly set to a maximum pressure. In another embodiment, by providing user input to the advancer 810, the medical professional may be enabled to manually push or retract the balloon catheter 806 from the second end 814. The medical professional may use a second hand to easily advance and retract the balloon catheter 806 to a desired location utilizing deftness and sensitivity.

The inflation control 811 may be selected utilizing a thumb or other finger of the operator. For example, by pressing the inflation control 811 embodied as a button, fluid may be pumped through the inflation port 812 into the balloon catheter 806 inflating one or more corresponding balloons. Releasing the inflation control 811 may deflate the balloon or release the pressure to the balloon catheter 806.

In another embodiment, the endoscopic sheath 800 may utilize a battery and small electric pump (not shown) to inflate and deflate the balloon catheter 806. The battery may be integrated into the handle 816 for easily changing or recharging the battery. The endoscopic sheath 800 may also include a recharging port for recharging the battery in the handle 816, whether permanent or removable. The endoscopic sheath 800 may be configured to pump liquid or air into the balloon catheter 806 to inflate or deflate the balloon.

In one embodiment, the endoscopic sheath 800 is configured to receive an inflation cartridge (not shown) in the inflation port 812 for inflating the balloon catheter with a liquid, such as saline. A new cartridge filled with fresh saline and a fresh balloon catheter 806 may be utilized for each medical procedure to ensure a sterile environment. For example, the inflation cartridge and balloon catheter 806 may be manufactured and pre-sealed utilizing known sterile and FDA approved processes. The liquid in the cartridge may also be utilized with the balloon catheter 806 or other fluid communications port or medium to irrigate, rinse, or flush a portion of the body of the patient (e.g. nasal cavity) or a lens of the endoscopic sheath 818. The volume of the inflation cartridge may vary between approximately 10 ml and 100 ml (or greater), although alternative volumes may also be utilized. The size may vary if the inflation cartridge is required to charge the balloon catheter 806 or other device with fluid before or during utilization or if the inflation cartridge is being utilized for irrigation.

In one embodiment, the inflation control 811 may be positioned on both sides of the handle 816 for ambidextrous control of inflating and deflating the balloon catheter 806. In one embodiment, the endoscopic sheath 800 may include a display (not shown) for indicating information related to the endoscopic sheath 800, such as the pressure applied to the balloon catheter 806 through the inflation port 812, an impingement or physical pressure applied to the balloon catheter 806 by the advancer, and so forth.

The bending section 808 may be manually, electrically, or mechanically controlled by a user control on or near the handle 816 or a body 818 of the endoscopic sheath 800 (see previous embodiments). The handle 816 allows the medical professional to more easily hold and operate the endoscopic sheath 800. In one embodiment, the handle 816 may be configured to pivot or rotate against the body 818 of the endoscopic sheath 800 to customize usage for the medical professional.

The second end 814 of the balloon catheter 806 may extend from an opening in the working port 804 at the rear portion of the endoscopic sheath 800. In one embodiment, the second end 814 is configured to loop back around to be connected to the inflation port 812. The excess or slack of the second end 814 may allow the balloon catheter 806 to be extended and retracted without having excessive amounts of balloon (or wire) near the medical professional during the procedure. For example, with a balloon sinuplasty procedure, the balloon catheter 806 may not need to extend more than 2-4 inches into the sinuses of the patient (before being inflated) once the endoscopic sheath 800 in inserted into the nasal cavity of the patient. In other procedures, the length of the second end 814 may vary to allow the balloon catheter 806 to reach the desired location before being inflated. In another embodiment, the inflation port 812 may be positioned at the bottom or back of the handle 816 or on die top of the body 818.

In another embodiment, the first end 809 of the scope port 802 may be configured to open to receive the endoscope from the first end 809. For example, the first end 809 of the scope port 802 may include an internal hinge and may snap open and shut. In another embodiment, the first end 809 may be a lens that may snap or screw onto the remaining portion of the scope port 802 to insert and remove the endoscope, such as a wireless endoscope. The diameter, length, and size of the scope port 802 may vary. For example, where the wireless endoscope is an extremely small 0.5 mm diameter and 1" long, the scope port 802 may correspond to the size the wireless endoscope. As a result, the scope port 802 may only extend along a portion of the working port 804 (such as the distance of the bending section 808.

Figure 9:
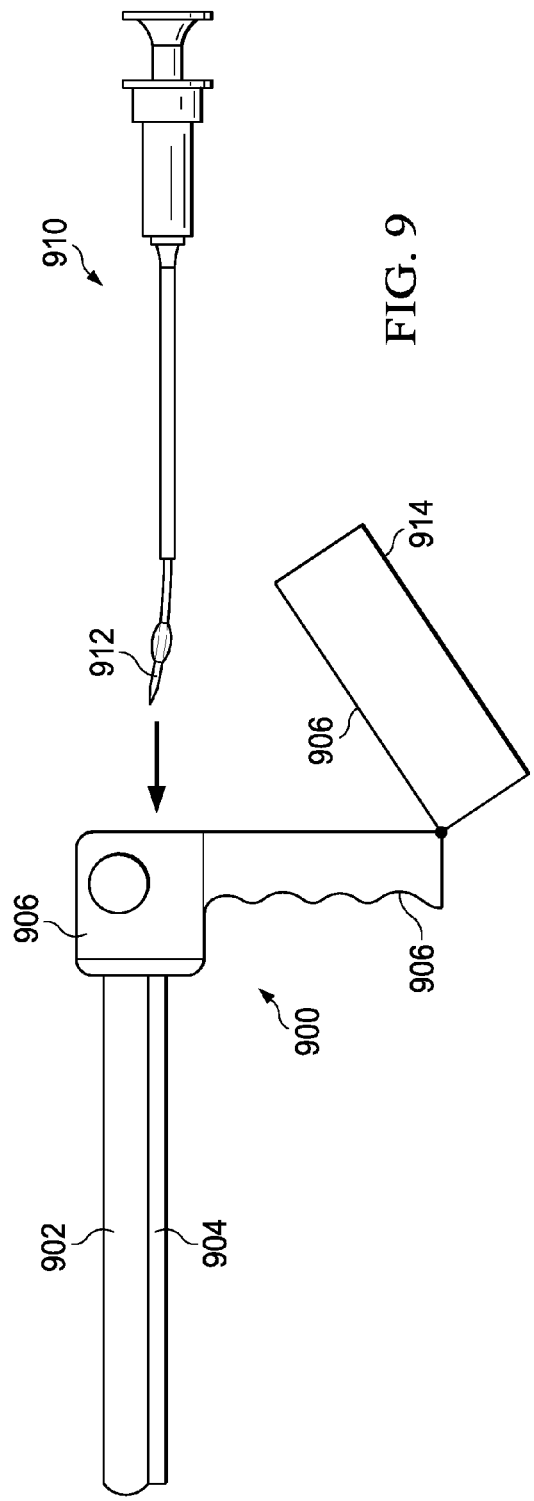
FIG. 9 is a schematic, pictorial representation of an endoscopic sheath receiving a balloon catheter system in accordance with an illustrative embodiment.

FIG. 9 is a schematic, pictorial representation of an endoscopic sheath 900 receiving a balloon catheter system 910 in accordance with an illustrative embodiment. The endoscopic sheath 900 may include some, many, or all of the components of the previous embodiments. In one embodiment, the endoscopic sheath 900 may include a scope port 902, a working port 904, a body 906, and an enclosing handle 906. The endoscopic sheath 900 is configured to partially or entirely encase the balloon catheter system 910.

Many existing balloon catheter systems may benefit from a handle or pistol type grip, such as the enclosing handle 906. The endoscopic sheath 900 is configured to receive dilation, video, irrigation, suction, abrasion, cauterizing, or balloon catheter systems, including, but not limited to, those produced by Acclarent, Entellus, ENTrigue, Olympus, or other similar medical device manufacturers.

In one embodiment, the enclosing handle 906 may be configured to open in a clam shell configuration to partially or substantially encompass and secure a portion of the balloon catheter system 910. The enclosing handle 906 may include includes tabs, clips, straps, or buckles for closing or securing the enclosing handle 906. The enclosing handle 906 includes cut-outs, holes, or ports for the tubes, structure, cables, and other components of the balloon catheter system 910 (not shown). For example, the balloon catheter system 910 may include a suction tube, inflation catheter or lumens, a wire, power cable or other components that extend from a rear portion 914 of the enclosing handle 906 during normal operation. The balloon catheter system 910 may extend beyond the end of the working port 904 allowing the balloon catheter system 910 to flex, pivot, rotate or otherwise be positioned within the working port 904. For example, a first end 912 of the balloon catheter system may be configured to bend, rotate, or pivot. The working port 904 is sized such that the balloon catheter system 910 may fully operate.

Additionally, the enclosing handle 906 may include cut-outs or controls that connect to or are integrated with the controls of the balloon catheter system 910. For example, if the balloon catheter system 910 includes a button, dial, adjustment point, or other interface or control, the enclosing handle 906 includes a similar interface that interacts with the interface of the balloon catheter system 910 to provide full functionality. For example, a button of the enclosing handle 906 may press a button of the balloon catheter system 910 when depressed by a medical professional. A cut-out may also allow controls and interfaces of the balloon catheter system 910 to be accessed when the endoscopic sheath 900 and balloon catheter system 910 are attached, docked, linked, or otherwise integrated.

Figure 10:
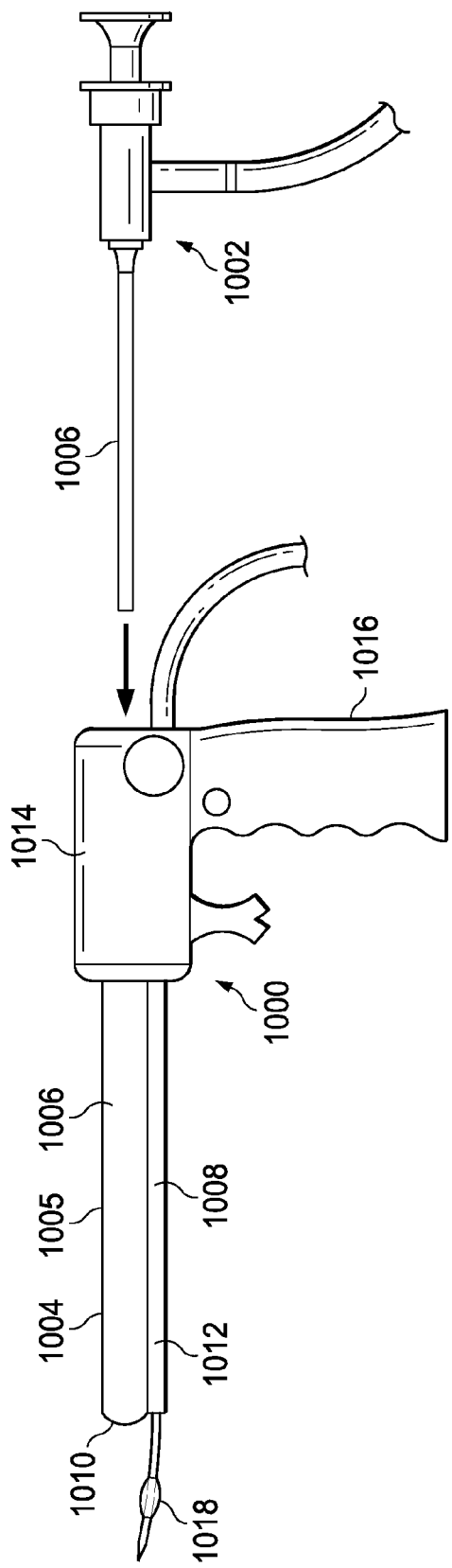
FIG. 10 is a schematic, pictorial representation of an endoscopic sheath receiving an endoscope in accordance with an illustrative embodiment.

FIG. 10 is a schematic, pictorial representation of an endoscopic sheath 1000 receiving an endoscope 1002 in accordance with an illustrative embodiment. The endoscope 1002 may be a medical device, endoscope, catheter, technology, or system, such as those sold by Acclarent. In one embodiment, the medical professional may insert and position the endoscopic sheath 1000 in the nose, cavity, or surgically created opening of the patient as previously described. In this embodiment, the endoscopic sheath 1000 includes an elongated frame 1005 enclosing a scope port 1006 and a working port 1008.

The lumens defined by the scope port 1006 and the working port 1008 are elongated to reach further into the nasal cavity of the patient toward the sinuses for performing various medical procedures. As previously described, the elongated frame 1005 may narrow slightly or significantly at a first end 1010 to facilitate gradual expansion of the nostrils and to reach further into the nasal cavities as the nasal cavities narrow.

The scope port 1006 (or the working port 1008) may be enclosed or sealed on the first end 1010. As a result, a non-medical scope, borescope, probe, or other instrument may be inserted into the endoscopic sheath 1000 without requiring an FDA-approved device or extensive sanitation. The sealed end of the lumen may be formed of a transparent glass or plastic for videoing or capturing visual content through the endoscopic sheath 1000. For example, the first end 1010 of the scope port 1006 may include a lens configured to enhance or not affect the video or images captured by the endoscope 1002. The lens may also be configured for zooming, providing microscopic views, focusing light for the endoscope 1002, or expanding or narrowing the viewing area (e.g., focal lens, fisheye lens, etc.).

The endoscopic sheath 1000 may include a bending section 1012. The bending section 1012 may be configured to correspond to the bending, rotation, or flexing properties of the endoscope 1002. The bending section 1012 may be flexibly directed toward a specific direction for reaching one or more of the sinuses. The bending section 1012 may be shaped before insertion into the nasal cavity of the patient. In another embodiment, the endoscopic sheath 1000 includes a control for moving the bending section 1012. The bending section 1012 of the endoscopic sheath 1000 may include corrugations (not shown) like a flexible straw for angling or positioning the scope port 1006 and working port 1008. For example, the endoscopic sheath 1000 may be manually bent or configured particularly at die corrugations to enhance performance of the medical procedure and the nose of the patient. Similarly, a portion of the frame of the endoscope 1002 may be directionally controllable, bendable, corrugated, or maneuverable for manually, mechanically, or electrically configuring the shape and direction of the endoscope 1002. The bending section 1012 of the frame may be sealed and completely or substantially waterproof like the rest of the endoscopic sheath 1000. The exposed or outer materials of the endoscopic sheath 1000 may include anti-microbial and anti-virus properties for preventing the potential spread of germs, viruses, diseases, microbes, or other unwanted biological contaminants. The endoscopic sheath 1000 may be configured as a disposable component for more easily meeting FDA requirements.

The endoscope 1002 may be positioned or inserted in either the scope port 1006 or the working port 1008 of the endoscopic sheath 1000. For example, the endoscope 1002 may be inserted into the scope port 1006 of the endoscopic sheath 1000 to view the nasal cavity (or other portion of the body) of the patient through the scope port 1006. The endoscope 1002 may be turned on and activated to begin generating and communicating video or image content to an external computing or communications device. The video or content signal may be communicated utilizing a wired or wireless connection.

The endoscope 1002 may be secured by the endoscopic sheath 1000 at a desired position and location selected by the medical professional. As previously described a body 1014 or handle 1016 of the endoscopic sheath 1000 may be configured to receive, attach to, integrate with, or be encompassed by the endoscopic sheath 100. In one embodiment, the endoscopic sheath 1000 and the endoscope 1002 may easily be inserted, separated, removed, or rotated. The video provided by the endoscope 1002 may be communicated to one or more other devices for guiding or informing the medical professional while performing a medical procedure.

The endoscope 1002 may provide both light and video within the nasal or body cavity or other orifice. The light and video may be utilized to position and utilize the endoscope 1002. For example, the video from the endoscope 1002 may ensure that a wire and balloon inserted through the working port 1008, such as a balloon catheter 1018, are guided into a selected sinus for performing a procedure, such as balloon sinuplasty. The balloon catheter 1018 or bougie may be controlled utilizing the endoscopic sheath 1000 as has been previously described including inserting, retracting, inflating, and deflating the balloon catheter 1018. In another embodiment, the endoscopic sheath 1000 may include one or more lights (not shown) for providing light for the endoscope 1002.

In another embodiment, the endoscopic sheath 1000 may include motorized or mechanical controls for positioning the first end 1010 or moving the bending portion 1012. The endoscopic sheath 1000 may be configured to operate with a flexible or bending endoscope. For example, the endoscopic sheath 1000 and the endoscope 1002 may pivot 90° and rotate 360°. In one embodiment, the endoscopic sheath 1000 includes a wireless or wired interface, servos, motors, wires, hinges, pivots, arms or other components for positioning the endoscopic sheath 1000. For example, a graphical user interface of an iPad, tablet, or other computing device may be utilized to vertically and horizontally position and angle the endoscopic sheath 1000 and endoscope 1002 to a desired position to illuminate tissue and provide video guidance of the endoscope 1002 and insertion of a wired balloon into one or more sinuses.

Figure 11:
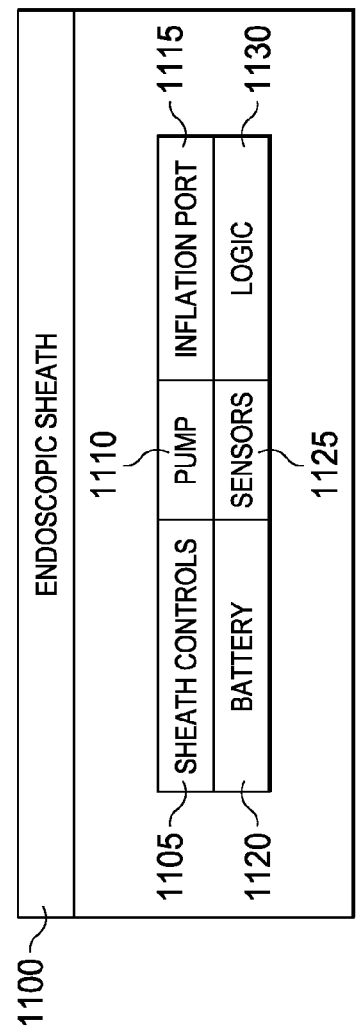
FIG. 11 is a block diagram of an endoscopic sheath in accordance with an illustrative embodiment.

FIG. 11 is a block diagram of an endoscopic sheath 1100 in accordance with an illustrative embodiment. In one embodiment, the endoscopic sheath 1100 may include sheath controls 1105, a pump 1110, an inflation port 1115, a battery 1120, sensors 1125, and logic 1130.

The sheath controls 1105 are the controls and interface that allow a medical professional to control all or portions of the endoscopic sheath 1100. A large portion of the functionality of the endoscopic sheath 1100 may be controlled by the medical professional pushing, pulling, and turning the endoscopic sheath 1100. The sheath controls 1105 may include any number of controls embodied in buttons, dials, grips, triggers, finger-controls, joysticks, levers, switches, trackball, touch sensor, motion sensor, accelerometer, and so forth. The sheath controls 1105 may include all mechanical embodiments, all electrical embodiments, or a combination thereof. In one embodiment, all or portions/features of the endoscopic sheath 1100 or a wireless endoscope may be controlled remotely.

In one embodiment, the sheath controls 1105 control advancement and retraction of components through the working port, such as a balloon catheter, wire, surgical tool, flexible endoscope, or other medical instrument. In another embodiment, the sheath controls 1105, when selected, may allow the components to be inserted or removed through the working port as a type of release (the components may be locked in place when the associated control is released).

The sheath controls 1105 may control motion of a tip or portion of the endoscopic sheath 1100 allowing the medical instruments, such as the portable endoscope and balloon catheter, to reach or be pointed at the correct location (e.g. sinus). The motion may be in a single direction or dimension or may be in multiple dimensions (e.g., x and y directions).

The sheath controls 1105 may also include a control for inflating and deflating a connected balloon catheter. The sheath controls 1105 may interact with the pump 1110 to apply pressure through the port, utilizing a gas or fluid. The sheath controls 1105 may both inflate the balloon catheter and deflate the balloon catheter. The sheath controls 1105 may also include controls for interfacing with the portable endoscope. In one embodiment, the sheath, controls 1105 may inflate the balloon of the balloon catheter to a designated pressure for a time period. The sheath controls 1105 or the logic may set the maximum inflation and impingement pressure for the balloon catheter before pressure is released or dissipated.

In another embodiment, the sheath controls 1105 may include a transceiver for sending a command to increase camera sensitivity, increase or decrease the light/illumination, or otherwise configure the endoscope wirelessly or through a physical connection to the endoscope.

The battery 1120 is a power storage device for driving operation of the endoscopic sheath 1100 if electrical power is required. The battery 1120 may power both the endoscopic sheath 1100 and a portable endoscope or other medical device utilized with the endoscopic sheath 1100. In one embodiment, the battery 1120 is removable from the endoscopic sheath 1120. In another embodiment, the battery 1120 is integrated with the body or handle of the endoscopic sheath 1100 and is rechargeable. The battery 1120 may be a high-powered energy storage device. For example, the battery 1120 may be a rechargeable or one-time use polymer battery, alkaline, zinc-air battery, lithium ion battery, thin film battery, ultra capacitor, fuel cell, piezo electric generator, or other capacitors or batteries being developed and known in the art. The battery 1120 may encompass a power port for powering the endoscopic sheath 1100 or charging the battery 1120 utilizing an adapter, power supply, or similar device.

The sensors 1125 provide feedback regarding utilization of the endoscopic sheath 1100. In one embodiment, the sensors 1125 include a pressure sensor to determine the pressure applied to inflate the balloon catheter. The pressure may be measured as applied by the pump 1120. The pressure may also be measured by the logic 1130 utilizing one or more formulas, fluid dynamics equations, instrument characteristics (e.g. type, length, diameter of the balloon catheter), and historical readings to determine the pressure at the balloon if substantially different. For example, the pressure applied by an actuator of the pump 1120 may be translated to determine a pressure applied at the balloon of the balloon catheter.

The sensors 1125 may also include a pressure sensor and motion sensor configured to determine the advancing or impingement pressure applied by the balloon catheter or bougie. For example, the sensor may measure the current and voltage being utilized by an electric motor to advance the balloon catheter or bougie. A motion sensor may also measure the rate of advancement or retraction of the balloon catheter or bougie. The various measurements may be utilized to determine the advancing pressure being applied by the catheter balloon, bougie, or other instrument to ensure that the patient is not injured during utilization of the endoscopic sheath 1100 and the associated medical instruments. For example, the pressure being inserted may correspond to a current being utilized by the electric motor. In another example, if the current increases and the balloon catheter or bougie is not moving the endoscopic sheath may determine the associated pressure. The sensors 1125 may be connected to a display or interface that communicates the relevant information and data measurements through visual, audio, tactile, verbal, or other output.

The logic 1130 may be configured to implement any number of criteria or thresholds. For example, the sheath controls 1105 may be configured to adjust the maximum pressure applied to the balloon catheter by the pump 1110 as well as the maximum force that may be applied by an electric motor or mechanical actuator to drive the motion of the balloon catheter, bougie, or other instrument. The logic 1130 may also include a processor and memory for implementing specific applications, scripts, or routines controlling the components of the endoscopic sheath 1100.

The logic 1130 or sheath controls 1105 may also include one or more displays, speakers, vibrators, or tactile feedback devices that indicate the pressure applied internally to the balloon catheter and at the tip or along the balloon catheter or bougie (externally). The pump 1110 may be an electric pump or a mechanical pump that enables the medical professional to inflate the balloon catheter. In one embodiment, the pump 1110 may be a mechanical pump that is driven by the medical professional squeezing a trigger to inflate the balloon catheter.

FIG. 12 is a schematic, plan view of a sheath balloon system 1200 in accordance with an illustrative embodiment. The sheath balloon system 1200 is a balloon system for performing balloon sinuplasty in accordance with an illustrative embodiment. The sheath balloon system 1200 is configured to perform balloon sinuplasty or other similar medical procedures. The sheath balloon system 1200 includes a balloon 1205, a probe 1210, a grip 1215, an inflation control 1220, an inflation port 1225, a first end 1230, a second end 1235, a directional control 1240, an advancer 1227, a fiber optic camera 1245, and an extension 1250.

In one embodiment, the probe 1210 includes internal lumens (not shown). For example, one or more inflation lumens may be utilized to communicate fluid to the balloon 1205 for inflating and deflating the balloon 1205. In addition, the probe 1210 may include a working port for conveying one or more medical instruments, such as the fiber optic camera 1245, a bougie, a balloon catheter, a suction device, an irrigation tube, or other component.

In one embodiment, the probe 1210 includes the balloon 1205 and may be attached or removed from the grip 1215. For example, the grip 1215 may include a clamp, latch, or other attachment mechanism and similarly the probe 1210 may include groves, ridges, or other components for being secured within the grip 1215. As a result, the sheath balloon system 1200 may be utilized repeatedly with different disposable balloons.

The probe 1210, or a portion of the probe 1210, may be controlled utilizing the directional control 1240. For example, wires or rods within lumens of the probe 1210 may be moved and controlled by the directional control 1240. In another embodiment, the probe 1210 may be flexible enough to be controlled by a component that is passed through a working port (not shown) of the probe. For example, movement of the fiber optic camera 1245 or a balloon catheter may be utilized to drive motion of the probe. The fiber optic camera 1245 may be a bronchoscope, colonoscope, duodenoscope, gastroscope, sigmoidoscope, rhinolaryngoscope, enteroscope, or other fiber optic image or video capturing device, such as those produced by Olympus, Pentax, Fujinon, ACMI, or Storz.

In one embodiment, the balloon 1205 may be an FDA compliant balloon as is known in the art. For example, the balloon 1205 may be configured for sinus dilation, heart or artery procedures, or other known medical inflation/deflation procedures. In one embodiment, the extension 1250 is a portion of the probe that communicates gas or fluid to inflate the balloon 1205 from the inflation port 1225. For example, the inflation port 1225 may be configured to receive an inflation cartridge that stores saline utilized to inflate the balloon 1205. In another embodiment, the inflation cartridge may utilize $CO_2$ or other inert or medically accepted gasses to inflate the balloon 1205. In one embodiment, fluid is pumped in response to selection of the inflation control 1220. For example, the inflation control 1220 may be an electric pump that pumps saline to the balloon 1205. In another example, the inflation control 1220 may be an elastomeric or flexible pump that the medical professional may repeatedly manually push on to pump fluid to die balloon 1205 and increase the pressure.

In another embodiment, the probe 1210 and extension may be a single piece that is threaded into the grip 1215. In one embodiment, the inflation lumen may be pre-charged with saline or another fluid to be inflated and deflated in response to selection of the inflation control 1220.

The advancer 1227 may be utilized to advance the fiber optic camera 1245, a balloon catheter, a bougie, or other medical instruments. For example, the advancer 1227 may be a thumb dial that proportionally drives the fiber optic camera 1245 in response to force or motion applied by the medical professional.

With reference now to both FIGS. 12 and 13, FIG. 13 is a schematic, plan view of a portion of the balloon sheath system 1200 including the first end 1230 in accordance with an illustrative embodiment. As shown, the probe 1210 may be bent manually or by operation of the sheath balloon system 1200. The fiber optic camera 1245 may be extended from the first end 1230 to further view additional portions of the patient's body as may be required for the medical procedure. In one embodiment, the fiber optic camera 1245 may be utilized with or integrated with a bougie or balloon catheter. For example, the fiber optic camera 1245 may be pushed into, through, or past a blockage to both clear the blockage and provide a view on the other side.

FIGS. 14 and 15 are schematic, perspective views of inflation cartridges 1400 and 1500 in accordance with an illustrative embodiment. The inflation cartridges 1400 and 1500 may be utilized with a sheath system or scope rather than requiring separate inflation devices and systems. For example, the inflation cartridges 1400 and 1500 may be inserted into the inflation port of the endoscopic sheath for purposes of inflating a balloon, providing irrigation, or suctioning bodily fluids. The inflation cartridges 1400 and 1500 may allow a medical procedure to be performed by a single medical professional, with less complexity.

In one embodiment, the inflation cartridges 1400 and 1500 may be utilized to store a fluid for inflating and deflating an inflatable component, such as a balloon of a balloon catheter. The inflation cartridges 1400 and 1500 may also be utilized to rinse or irrigate a wound, tissue, cavity, or other body part internal or external. For example, the inflation cartridges 1400 and 1500 may be pre-charged or loaded with saline. However, the inflation cartridges 1400 and 1500 may also be loaded with one or more fluids (or mixtures of fluids) such as, isotonic glycine, nitroglycerin, markers, sorbitol, iodine, hydrogen peroxide, sterilized water, antibiotic mixtures, and other reagents. In another embodiment, the inflation cartridge 1400 and 1500 may be charged with an inert or medically approved gas, such as carbon dioxide, oxygen, argon, or helium.

In one embodiment, the inflation cartridges 1400 and 1500 may be configured to be compressed and expanded to both expel and suction gas or fluid. For example, an actuator may be connected to the inflation cartridges 1400 and 1500 to perform these functions. In another embodiment, the fluid or gas in the inflation cartridges 1400 and 1500 may be expelled by a pump pumping in fluid or gas into the inflation cartridges 1400 and 1500. In another embodiment, the fluid or gas may be removed from the inflation cartridges 1400 and 1500 by a pump for communication to another device or communications medium, such as a balloon cartridge or tubing. The inflation cartridges 1400 and 1500 may include any number of ports, nozzles, filters, and membranes for communicating fluid or receiving fluids or gases.

The inflation cartridges 1400 and 1500 may be configured to be single use components that may be inserted into a sheath, endoscope, or other system as herein described or as are currently used in the art. In one embodiment, the inflation cartridges 1400 and 1500 may be compressed by a pump or motor to propel the fluid from the inflation cartridges 1400 and 1500. Additionally, the inflation cartridges 1400 and 1500 may be decompressed to suction the fluid back. The inflation cartridges 1400 and 1500 may be reduced in size (i.e., 0.5-2 in diameter) for integrating within a handle or body of any of the devices or systems described in the illustrative embodiments.

The inflation cartridge 1400 includes a body 1402, a nozzle 1404, a top 1406, a rod 1408, and a seal 1410. The top 1406 may be connected to the seal 1410 by the rod 1408. The seal 1410 forms an airtight and watertight seal with the body 1402. The seal 1410 may move within the body 1402 to expel the fluid through the nozzle 1404. The endoscopic sheath may include a support, piston, rod, collar, arm, or sleeve for exerting forces on the top 1406 (both toward and away from the nozzle 1404) to expel or suction fluid from the body 1402 through the nozzle 1404. For example, the inflation cartridge 1400 may be formed of an FDA approved plastic for holding the fluid or gas.

In one embodiment, the nozzle 1404 may be sealed and perforated to keep the saline fresh and unexposed to outside elements until the inflation cartridge 1400 is used. For example, once the medical professional is ready to use die inflation cartridge 1404, a plastic or tinfoil seal may be removed from the nozzle 1404 or an end of die nozzle 1404 may be cut off, broken, breached, screwed off, or removed.

The nozzle 1404 may function as a port or outlet for interfacing or communicating fluid with a balloon catheter, tube, or other similar component. For example, the nozzle 1404 may be cylindrical or pointed for breaking or puncturing a seal of a balloon catheter to fill the balloon with a fluid or gas thereby inflating the balloon. The nozzle 1404 or endoscopic sheath may also include a clamp, spring, buckle, coupler, or other securing mechanism known in the art for interfacing or connecting the inflation cartridge 1400 and other components, such as the balloon catheter. The balloon catheter may include a sleeve or differently sized end for being secured over or within the nozzle 1404.

In one embodiment, the body 1502 may include a ridge or tab (not shown) extending from the body 1502. The ridge may be utilized to insert or position the inflation cartridge 1500 in a medical instrument. In addition, the ridge may allow the inflation cartridge 1500 to be rotated for connecting or detaching the inflation cartridge 1500 to the medical instrument.

With reference to FIG. 15, the inflation cartridge 1500 may also include a body 1502, a nozzle 1504, and a recessed seal 1506 with indentations 1508. The inflation cartridge 1500 may have a reduced footprint for utilization in an endoscopic sheath. In one embodiment, the indentations 1508 are L-shaped recesses for receiving tabs or teeth of the driving mechanism of the endoscopic sheath or other medical instrument. Thus, tabs of a piston, actuator, or pump may be inserted into the indentations 1508 and then the body 1502 and seal 1506 may be rotated slightly to engage the tabs within the indentations 1508. For example, the recessed seal 1506 may be driven by a tabbed piston, actuator, or rod of the endoscopic sheath that is driven by user input, selections, or commands received from the medical professional.

In one embodiment, the seal 1506 is a plunger that may be moveably extended through the cavity formed by the body 1502 of the inflation cartridge. The seal 1506 may include a grommet, washer, gel, or other sealing component providing a liquid and airtight seal. The seal 1506 may be surrounded about a diameter or periphery by the sealing component.

In another embodiment, the seal 1506 may include threads for connecting the seal 1502 to the piston, rod, or drive mechanism of the endoscopic sheath or other instrument, in yet another embodiment, the actuator driving motion of the recessed seal 1506 may include teeth and the endoscopic sheath may include indentations. A fully compressed inflation cartridge 1500 may be driven away from the nozzle 1504 to provide suction or extract fluid, tissue, or other organic samples. The fluid samples may then be analyzed or processed as needed. In other embodiments, the body 1502 may utilize three dimensional shapes other than cylinders as is shown in FIGS. 14 and 15, such as ellipses, rectangles, pentagons, or octagons.

FIG. 16 is a schematic, plan view of a connector 1600 in accordance with an illustrative embodiment. The following description is applicable to any of the connectors of FIGS. 16-19. The connector 1600 may be a stand-alone device or may be integrated with the systems and devices described herein, such as portable endoscopes, endoscopic sheaths, fiber optic cameras, and balloon catheters.

The connector 1600 is configured to connect two or more medical instruments or other devices together for utilization. In one embodiment, the connector 1600 may be configured to connect a portable endoscope and balloon catheter system. In another embodiment, the connector 1600 may be configured to flexibly connect an endoscope and a balloon catheter. However, the connector 1600 may be utilized with any number of medical or non-medical devices. Using the connector 1600, the medical professional may not need to hold the devices with two different hands or require the assistance of a third-party. As a result, medical professionals may be able to work more independently in a number of different settings or environments. In one embodiment, for nasal applications the connector 1600 may be configured to connect devices with a diameter or width of between 0.5 mm-1.5 cm in diameter. However, the size or diameter of the connector 1600 may vary based on the application.

In one embodiment, the connector 1600 includes a first clamp 1602, a second clamp 1604, and a support 1606. The first clamp 1602 and the second clamp 1604 are connected by the support 1606. The length of the support 1606 may vary based on the application. For example, where two medical instruments connected by the connector 1600 are inserted into a nostril of a patient, the support 1606 (or distance) between the first clamp 1602 and the second clamp 1604 may be extremely short. The width of the support 1606 may vary based on die amount of flexibility required for the connector 1600. For example, the support 1606 may be narrow for applications in which the first clamp 1602 and the second clamp 1604 need to move or flex independently. In an alternate embodiment, the first clamp 1602 may be directly coupled to the second clamp 1604 without need for the support 1606.

In one embodiment, the support 1606 may be very rigid to prevent torsion or rotation of the first clamp 1602 and the second clamp 1604. For example, the support 1606 may be formed of a rigid plastic. In another embodiment, the support 1606 may be flexible to support slight independent movement of the first clamp 1602 and the second clamp 1604. For example, the support 1606 may be formed of silicon and may allow and endoscope and a balloon catheter to move and rotate independently while still being connected by the connector 1600. The materials utilized for the clamps 1602 and 1604 and the support 1606 may differ based on the application.

In one embodiment, die first clamp 1602 and second clamp 1604 are open ended clamps that are configured to secure medical instrumentation by proper sizing and the corresponding friction. In other embodiments, the clamps 1602 and 1604 may include bands, buckles, or clips for further securing the clamps 1602 and 1604 around the medical instruments. In another embodiment, the internal surfaces of the first clamp 1602 and the second clamp 1604 that contact devices, such as medical instrumentation, may have a non-slip, neutral, or slippery surface. For example, if two medical instruments need to be closely affixed, the internal surfaces of the clamps 1602 and 1604 may include a non-slip material, or integrated structures. For example, the internal surfaces may include small protuberances, patterns, or adhesives that grip the medical instruments. As a result, motion and rotation of one instrument may result in a corresponding motion and rotation of the interconnected instrument.

In another example, two medical instruments may need to be closely affixed, but need to be able to slide within the clamps 1602 and 1604. As a result, the internal surfaces of the clamps 1602 and 1604 may be formed of a low friction or slippery material. For example, the internal surfaces may include Teflon or may be lubricated before use.

In one embodiment, the connector 1600 may be molded from a single piece of plastic, rubber, silicon, composite or other material. For example, the connector 1600 may be composed of medical grade plastic. The connector 1600 may be disposable or reusable for connecting various devices.

The first clamp 1602 and second clamp 1604 are configured to snap onto the medical instrument or device. The diameter of the first clamp 1602 and the second clamp 1604 correspond to the diameter of specific medical instruments. The connector 1602 may be manufactured in any number of permutations and tolerances to fit an unlimited number of sizes and shapes of medical instruments. For example, the first clamp 1602 may also be elliptically shaped for a balloon catheter that utilizes an ellipse as a cross-sectional shape. To use the connector 1600, the medical professional may simply snap the first clamp 1602 and second clamp 1604 onto medical instruments at a preferred location. In addition, the medical professional may utilize multiple connectors at once if the medical instruments are quite long or additional support is required.

FIG. 17 is a schematic, plan view of a connector 1700 in accordance with another illustrative embodiment. The connector 1700 may be configured to slide onto medical instruments. The connector 1700 may include clamps 1702 and 1704. The clamps 1702 and 1704 may be closed ended or looped for securing the medical instruments. In one embodiment, the clamps 1702 and 1704 may be sized nearly identically or slightly smaller than the medical instruments requiring the clamps 1702 and 1704 to be stretched slightly to be fit onto the medical instruments. In addition, a support 1706 may be of reduced length and width. In one embodiment, if silicon is used for the support 1706, the medical instruments secured by die clamps 1702 and 1704 may have more play or give in their interconnection. Additional play or flexibility may be required for different types of medical procedures or technical implementations. The connector 1700 may be utilized in any number of scenarios or configurations. In one embodiment, the connector 1700 may be utilized to connect a flashlight, such as a Maglite®, to a tool, such as a ratchet or screw driver.

In one embodiment, the clamps 1702 and 1704 may include a ratchet, buckle, or strap mechanism for tightening or loosening the clamps 1702 and 1704 (or decreasing and increasing the diameter).

FIGS. 18 and 19 are a schematic, front view and side view, respectively of the connector 1600 of FIG. 16 securing a balloon catheter system 1608 and a portable endoscope 1610 in accordance with an illustrative embodiment. A portion of the balloon catheter system 1608 and portable endoscope 1610 are shown in FIGS. 18 and 19 for purposes of simplicity.

As shown by the side view of FIG. 20, in another embodiment, multiple connectors 2002 and 2004 may be interconnected by a support 2006. Any number of supports may be positioned between or above the clamps of the connectors 2002 and 2004. The support 2006 provides additional stability when linking medical instruments. In addition, the support 2006 may prevent the clamps of the connectors 2002 and 2004 from corning unattached. The support 2006 may provide additional rigidity and may better stabilize multiple medical instruments. In addition, the support 2006 may prevent the medical instruments from touching to prevent chipping, wear, or unnecessary noise. The support 2006 may be a connection member, such as a rod, column, link, or stabilizer corresponding to the length and width of the supports that are shown in other embodiments.

Figure 21:
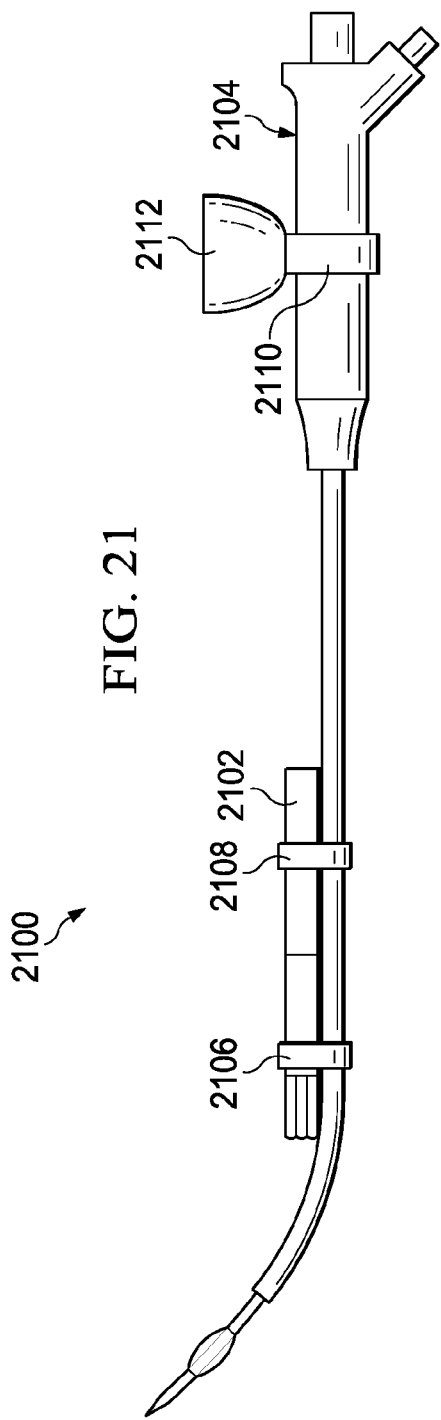
FIG. 21 is a schematic, plan view of a balloon catheter system in accordance with an illustrative embodiment.

FIG. 21 is a schematic, plan view of a balloon catheter system 2100 in accordance with an illustrative embodiment. In one embodiment, the balloon catheter system 2100 includes a portable endoscope 2102 (as is herein described) attached to the balloon catheter 2104 by connectors 2106 and 2108. In addition, a handle 2112 may be attached to the balloon catheter 2104 utilizing a clamp 2110.

In one embodiment, the balloon catheter 2104 is enhanced by the addition of the portable endoscope 2102. As a result, the medical professional may see video and image content while moving and positioning the components of the balloon catheter 2104 based on the real-time video signal communicated from the portable endoscope 2102.

The handle 2112 provides an enhanced ergonomic grip for holding, moving, and positioning the balloon catheter 2104. In one embodiment, the handle 2112 may attach to the balloon catheter 2104 utilizing the clamp 2110. The clamp 2110 may be a strap, radial clamp, band, or snap together band that may be configured (or is custom designed) for the balloon catheter 2104. The handle 2112 may attach from the top (as shown), side, or bottom of the balloon catheter 2104. In one embodiment, the handle 2112 is shaped as sphere, or partial sphere. In other embodiments, the handle 2112 may be triangularly shaped. The attachment of the portable endoscope 2102 and the handle 2112 may turn any existing medical instrument such as a sinus dilation tool or sinus balloon catheter, into a more complete and robust system. In addition, the handle 2112 may be an inflation handle as is described in FIG. 31. The handle 2112 may also be configured to include controls for any portion of the balloon catheter system 2100. For example, the handle 2112 may include a control for rotating or zooming a camera within the portable endoscope 2102.

Figure 22:
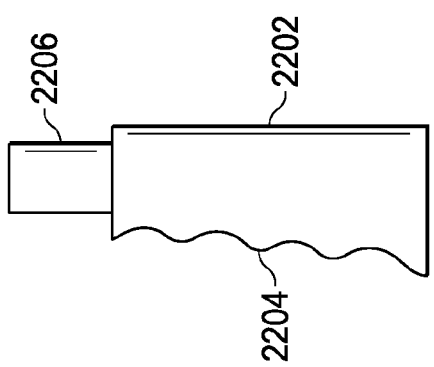
FIG. 22 is a schematic, plan view of a handle in accordance with an illustrative embodiment.

In the embodiment shown in FIG. 22, a handle 2202 includes a grip 2204. The handle 2202 may be attached to a medical instrument or other device from any position utilizing a clamp 2206. In one embodiment, the handle 2202 may be hinged or snap together in pieces (as has been previously described) to partially encompass a medical instrument or other device. The handle 2202 may be attached to a medical instrument to provide a medical professional an enhanced grip and more ergonomic utilization of a medical instrument. The grip 2204 may include protuberances, ribs, or may be rubberized or include another non-slip surface for working in difficult conditions.

In one embodiment, the handle 2202 is configured to include or house any or all of a battery, a pump, logic, sensors, or an inflation port (not shown). The handle 2202 may also be configured to receive an inflation cartridge, such as the inflation cartridge 1500 of FIG. 15. For example, a balloon catheter may be connected to an inflation port to inflate and deflate a balloon. The pump may be configured to drive a fluid or gas to inflate the balloon or provide irrigation. For example, the pump may be configured to inflate the balloon utilizing air from die local environment. In another embodiment, the handle 2202 may receive a AAA or rechargeable battery from a bottom portion of the handle 2202, an inflation cartridge may be loaded into a side of the handle 2202 and saline may be driven into the catheter by compressing or pumping fluid from the inflation cartridge.

Figure 23:
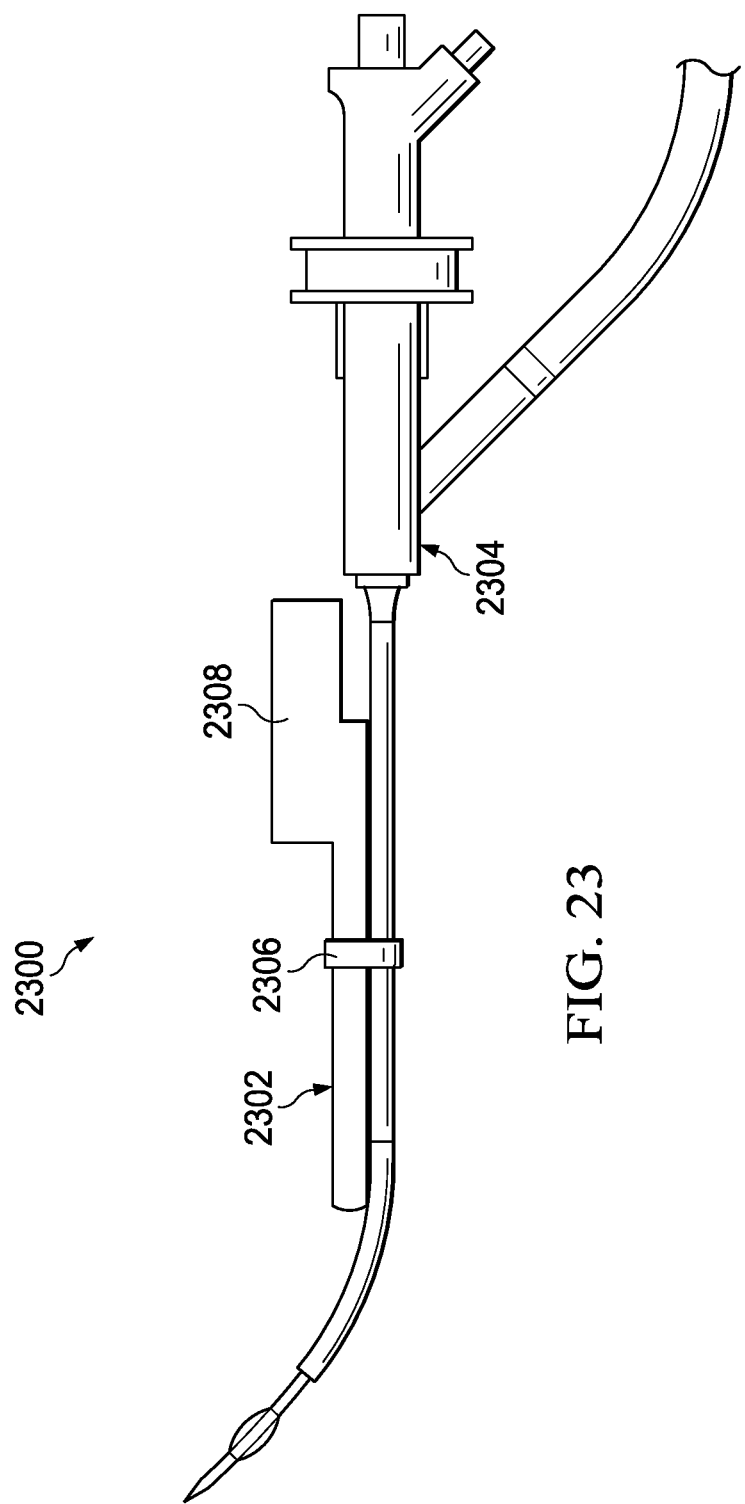
FIG. 23 is a schematic, plan view of a balloon catheter system in accordance with an illustrative embodiment.

FIG. 23 is a schematic, plan view of a balloon catheter system 2300 in accordance with an illustrative embodiment. In one embodiment, the balloon catheter system 2100 includes a portable endoscope 2302 attached to the balloon catheter 2304 by connector 2306. The portable endoscope 2302 may further include an extension 2308.

In one embodiment, die extension 2308 may be utilized to manipulate die portable endoscope 2302 or the balloon catheter system 2300. For example, the portable endoscope 2302 may be moved back and forth or rotationally positioned along the length of the balloon catheter system 2300. In addition, the extension 2308 may enclose the transceiver and battery (not shown) of the portable endoscope 2302. The extension 2308 may be larger than the portion of the portable endoscope 2302 that may be inserted into the patient's body. As a result, the transceiver may be positioned to more effectively communicate with external devices and the battery size may not be as limited due to the size limitations of the other portions (e.g., a portion inserted into the body of the patient) of the portable endoscope 2302.

FIG. 24 is a schematic, cut-away view of a video bougie 2400 in accordance with an illustrative embodiment. In one embodiment, the video bougie 2400 may include a body 2402, a tip 2404, a fiber optic camera 2406, and a relief port 2408. The video bougie 2400 may be sized to be utilized for various medical procedures. For example, the video bougie 2400 may be utilized to clear a blockage in an artery or organ, such as a colon. In another embodiment, the video bougie 2400 may be inserted into the sinuses of a patient to dilate and expand the sinuses by partially or fully inserting the tip 2404 and body 2402 of the video bougie 2400.

In one embodiment, the video bougie 2400 may include an internal lumen 2410 for receiving the fiber optic camera 2406. The lumen 2410 and fiber optic camera 2406 may be formed of a material and sized such that the fiber optic camera 2406 may be slid into video bougie 2400. For example, the lumen 2410 may be Teflon coated for receiving the fiber optic camera 2406. However, the lumen 2410 may utilize any number of low friction materials or mechanisms (e.g., rollers, bearings, etc) that may facilitate the video bougie 2400 receiving a camera or other instrument. In another embodiment, the video bougie 2400 may be manufactured with the fiber optic camera 2406 or other surgical instrument running through the lumen 2410. The diameter of the lumen 2410 may correspond to a designated fiber optic camera 2406. The types and configurations of fiber optic cameras are well known in the art and additional details are not required.

Although nor shown, the video bougie 2400 may include a lens at the tip 2404 for enabling or enhancing the operation of the fiber optic camera 2406. In another embodiment, the tip 2404 may include one or more stops or supports for preventing the fiber optic camera 2406 from slipping past the end of the tip 2404. In another embodiment, the tip 2404 may narrow slightly to secure the fiber optic camera 2406. In another embodiment, the fiber optic camera 2406 and the lumen 2410 may include indentations or stops for stopping the fiber optic camera 2406 flush with the tip 2404 of the video bougie. The video bougie 2400 and fiber optic camera 2406 may be waterproof and water tight for preventing fluids from entering any or all portions of the video bougie 2400.

In one embodiment, the tip 2404 may be open allowing the fiber optic camera 2406 or surgical instrument to pass the tip 2404 of the video bougie 2400. An open tip may allow a medical professional to ascertain whether to open a blockage with the video bougie 2400 by passing a forward or reverse looking fiber optic camera 2406 beyond the tip 2404 of the video bougie 2400 before proceeding with the procedure.

In one embodiment, the video bougie 2400 may include the relief port 2408 that allows air or fluid (e.g., lubricant, graphite, etc) pushed along the lumen 2410 to be released during insertion of the fiber optic camera 2406. A plug or stop may be inserted into the relief port 2408 once the fiber optic camera 2406 is properly positioned for waterproofing and sterility.

FIG. 25 is a schematic, cut-away view of a video bougie 2500 in accordance with another illustrative embodiment. In one embodiment, the video bougie 2500 may include a body 2502, a tip 2504, and a fiber optic camera 2506. The video bougie 2500 illustrates a different shaped tip 1504. The size of the fiber optic camera 2506 may also vary based on the application. The angle, shape, and curve of the video bougie 2500 may vary based on the type of application. For example, the video bougie 2500 may be small enough to fit into an artery to clear a blockage and the video bougie 2400 of FIG. 24 may be utilized to perform sinus surgery. The video bougie 2500 or the fiber optic camera 2506 may also include cables or wires for controlling the direction or motion of the tip 2504, the video bougie 2500, or the fiber optic camera 2506.

In one embodiment, the video bougie 2500 may be configured to be disposable. For example, the fiber optic camera 2506 integrated or inserted within the video bougie 2500 may be an extended fiber extension that is connected to the much larger image control and processing components of the fiber optic camera 2506. The video bougie 2500 and fiber optic strand may be inserted, snapped, screwed, or otherwise attached to the main body of a fiber optic camera. In one embodiment, the all or a portion of the video bougie 2500 may be inflated to perform a procedure. For example, a tip portion of the video bougie 2500 may increase in diameter when inflated or the entire video bougie 2500 may be inflated with a fluid.

Figure 27:
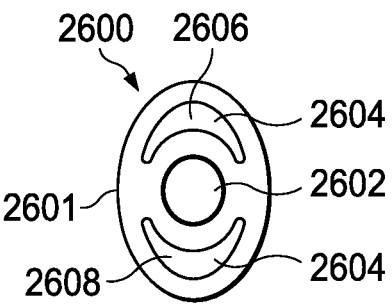
FIGS. 27 and 28 are schematic, front views of a portable endoscope in accordance with an illustrative embodiment.
Figure 28:
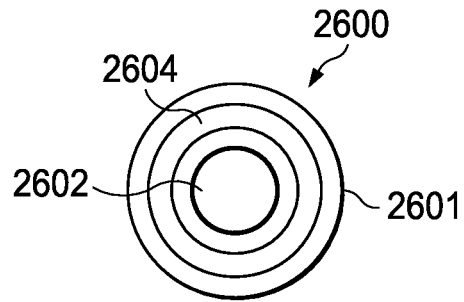

Turning now to FIGS. 26-28, a schematic, pictorial representation of a portable endoscope 2600 is shown in accordance with illustrative embodiments. An endoscope is an instrument that may be introduced into the body of an individual or patient to give a view of internal parts. The portable endoscope 2600 may be utilized in very small spaces and may be easier to use than existing endoscopes. Existing endoscopes are generally bulky and not ergonomically shaped and may require two or more medical professionals to operate effectively (e.g., a doctor and nurse).

In one embodiment, the portable endoscope 2600 is a wireless scope that is condensed into a reduced footprint or size. The portable endoscope 2600 may also be referred to as a wireless endoscope. The portable endoscope 2600 may be utilized by a single medical professional or positioned a single time or as needed (e.g., within a nasal guide) to free up hands of the medical professional. The nasal guide may be utilized to stabilize instruments inserted into a user's nose or other orifices and is described in the related applications. The portable endoscope 2600 may utilize any number of wireless signals to communicate content to computing and/or communications devices.

The portable endoscope 2600 may be cleaned for repeated use or may be a disposable one-time use portable endoscope 2600. The portable endoscope 2600 may also be utilized with a rigid or flexible cover that may be disposed of after being used. The portable endoscope 2600 may have a wand or cylindrical-shape for easy handling by a medical professional. In another embodiment the portable endoscope 2600 may be a small diameter cylinder that may be short or long in length depending on the application. The portable endoscope 2600 may have a diameter or cross-sectional measurement of between 0.5 mm to 5 mm, although the diameter may vary widely, both larger and smaller, depending on the particular application. For laparoscopic and other similar procedures, the diameter may vary between 5-50 mm in size.

The portable endoscope 2600 may be a stand-alone device or may be utilized or integrated with the endoscopic sheath and other components or embodiments as are herein described. For example, the portable endoscope 2600 may be built into one or more of the lumens of an endoscopic sheath 2620 or a nasal guide. The portable endoscope 2600 may also be attached to or inserted into the endoscopic sheath 2620.

As exemplified in the schematic front views of FIGS. 27 and 28, the portable endoscope 2600 may be shaped as a circle, rounded square, oval, ellipse, rounded triangle, or any other shape. The portable endoscope 2600 may be utilized for any number of medical or non-medical procedures or examinations that are known in the art. In one embodiment, the portable endoscope 2600 is configured to be received by an opening, lumen, or port of die endoscopic sheath 2620 as herein described.

The portable endoscope 2600 may be inserted to a required depth and positioned to display a video or image content to the medical professional. In one embodiment, friction, tight tolerances, opposing magnets, or interference fittings of the opening and external dimensions of the portable endoscope 2600 may be utilized to secure the portable endoscope 2600 in the endoscopic sheath 2620. In another embodiment, the portable endoscope 2600 may include a positioning motor or drive mechanism (e.g. rail drive, track drive, hydraulic drive) for moving the portable endoscope 2600 in and out, rotating the portable endoscope 2600, angling a camera 2602 of the portable endoscope 2600 or otherwise positioning the portable endoscope 2600 within the examined space. The same positioning feature may be performed for the camera 2602 without moving the portable endoscope 2600.

In one embodiment, the portable endoscope 2600 may include the camera 2602, a light 2604, a transceiver 2606, and a battery 2608. The portable endoscope 2600 may be enclosed in a case 2601. In one embodiment, the case 2601 is a waterproof framework completely sealing in and securing the components of the portable endoscope 2600. The case 2601 may include any number of seals and watertight connections ensuring that the portable endoscope 2600 may be utilized multiple times without damage from fluids. For example, the case 2601 may be formed entirely of a metal, polymer, plastic, or glass. In another embodiment, different components and materials may be fused together. For example, the main body of the case 2601 may be formed of stainless steel with a glass end or lens for the light 2604 to shine through and the camera 2602 to retrieve video images.

In another embodiment, both the case 2601 and the components of the portable endoscope 2600 may be flexible for utilization in various positions where bending or flexing is required. For example, die case 2601 may be composed of rubber or plastic with indentations or corrugation to support bending. Similarly, the components of the portable endoscope 2600 may be formed of, printed on, or manufactured utilizing flexible circuits and electronics, such as thin film transistors, organic light emitting diodes, flexible plastic substrates, flexible printed circuits, flexible flat cables, and so forth. The portable endoscope 2600 may include motors, cables, actuators, hinges, or other drive mechanisms for bending (e.g. 5-360° or more).

In one embodiment, the case 2601 includes the contacts, interfaces, wires, or busses for each of the internal electrical components. For example, the camera 2602 or light 2604 may contact a communications bus integrated within the frame or case 2601 for transmitting the video or image signal to the transceiver 2606 for transmission. The light 2604 may also include an interface for communicating video signals from the camera 2602 to the case 2601 or directly to the transceiver 2606.

In one embodiment, the bus for sending and receiving video or commands may be insulated or the case 2601 may include a designated space ensuring that none of the components contact the bus. Likewise, a wire or power conduit integrated within the case 2601 may communicate an electrical energy signal from the battery 2608 to the transceiver 2606, light 2604, or camera 2602. In another embodiment, the electrical components may be serially connected in the positioned order for both powering the components and communicating a video signal (and command signals as needed). In yet another embodiment, each of the electrical components may have a separate connection to the battery 2608 or transceiver 2606 to prevent cross-talk, interference, or other undesirable electrical effects.

A first end 2603 of the case 2601 may include or be formed of a lens or transparent plastic cover (not shown) focusing or allowing light to be acquired as video content by the camera 2602. Any number of lenses (not shown) may be utilized depending on the medical procedure being performed. For example, the lens may be a simple convex, biconvex, plano-convex, positive meniscus, negative meniscus, plano-concave, macro, zoom, apochromat, process, fisheye, stereoscopic, infrared, ultraviolet, swivel, biconcave, etc. lens. The lens may also be selected to prevent fluids from accumulating on the camera 2602 and light 2604 blocking the view of the relevant site. In another embodiment, the endoscopic sheath 2620 may include a lens at the first end 2603 for generating a video signal utilizing the reflected light emitted by the light 2604. The portable endoscope 2600 and the endoscopic sheath 2620 may be configured to abut one another such that the images captured by the camera 2602 are clear. The lens may also be utilized to provide magnification, zooming abilities, or a focusing component.

In one embodiment, the camera 2602 is a condensed digital video camera configured for wirelessly communicating the video content through the transceiver 2606. The camera 2602 may be configured to capture video in response to the output of the light 2604 which may broadcast visible light, specific spectrums, infrared, ultrasound, ultra violet, x-ray, gamma ray, or other electromagnetic or non-electromagnetic imaging. The camera 2602 may also be configured to capture still images in any of the described spectrums. In one embodiment, the light 2604 may be a fiber optic light that is powered by external sources. Any kind of digital or fiberoptic imaging or viewing device may be used may be used for the camera 2602 and the light 2604. In one embodiment, the camera is a charge coupled device (CCD) camera, such as a CMOS camera, composed of multiple stacked and interconnected semiconductor layers. The camera 2602 may be configured or selected to correspond to, pick-up, or capture the type of light 2604 inserted or installed in the portable endoscope 2600. The camera 2602, portions of the portable endoscope 2600, or the endoscopic sheath 2620 may be manually or remotely controllable. For example, the camera 2602 may include a swivel lens that rotates to give unique perspectives and camera angles. The lens or camera 2602 may also be configured to protrude from or extends from the portable endoscope 2600 to enhance visibility and flexibility of the portable endoscope 2600. In another embodiment, the camera 2602 may be a fiber optic camera.

The camera 2602 may utilize any number of electronic or even vibrational spectra for chemical analysis, oximetry, disease classification, and molecular microscopy. For example, the camera 2602 may also be configured to include features of a microscope. In addition, diffuse reflection, fluorescence reflectance (fluorescence spectroscopy), Raman reflectance (Raman spectroscopy), and absorption may be observed, measured, or recorded by the camera 2602. The wavelength or spectrum produced by the light 2604 may affect the light 2604 and camera 2602 selected for the portable endoscope 2600. The camera 2602 may be configured to produce 1-D spatial information utilizing a single wavelength or spectrum, 2-D spatial information utilizing wide-field spectroscopy/hyperspectral imaging, and 3-D spatial information utilizing tomography. The camera 2602 may be selected for a particular light 2604 or based on characteristics of the camera 2602 or generated video signal including resolution, intensity, frame rate, signal-to-noise ratio (SNR), peak SNR, noise immunity, timing, scanning, and so forth.

The video captured by the camera 2602 may be transmitted directly or indirectly to the wireless device 2612 or computing device 2614. For example, the portable endoscope 2600 may wirelessly communicate with the computing device 2614 through a network 2616. The network 2616 may utilize a communication standard, such as 802.11_ (e.g., 802.11n). The direct or indirect communications may represent Bluetooth, ZigBee, near field communication (NFC), WiFi, ultra-wideband, wireless USB, infrared, wireless local area network (WLAN), WiMAX, proprietary standards, or other radio frequency signals whether analog or digital that may be utilized to communicate a video signal. Any number of FCC, FDA, IEEE, ISO, CEN, ETSI, ARIB, ANSI, or IEC approved communications protocols or standards may also be transmitted by the transceiver 2606. The transceiver 2606 as well as the transceiver (not shown) of the wireless device 2612 or computing device 2614 may include any of the components necessary for communicating utilising these standards. Indeed, the types of wireless or wired standards or methods of communication are numerous.

In one embodiment, an antenna (not shown) may be built into the transceiver 2606. The antenna may also be a wire antenna that extends from a second end 2605 of the case 2601 (and from the endoscopic sheath 2620) to establish a stronger wireless signal. In another embodiment, the case 2601 may be connected to the transceiver 2606 allowing all or portions of the case 2601 to act as the antenna for the transceiver 2606.

The video or image signal may be received and displayed by the wireless device 2612 or computing device 2614 in real-time. The video signal may be formatted before or after being sent from the portable endoscope 2600. In one embodiment, the portable endoscope 2600 may include a processor, ASIC, FPGA, or other logic for managing the portable endoscope 2600 and processing the video signals. The video may be compressed in a raw or formatted state for communication by the transceiver 2606. For example, the video content may be packetized and communicated with or without encryption. Error detection and known packet analysis, processing, decryption, and other similar steps may be performed by a receiving device.

In one embodiment, the portable endoscope 2600 may include a memory for storing the video content for subsequent analysis, review, documentation, training, or educational purposes. For example, the computing device 2612 and wireless device 2614 may be unavailable and the medical professional may want to save video content for subsequent analysis. In another embodiment, the video may be recorded by the wireless device 2612 or computing device 2614 for the same reasons. The portable endoscope 2600, wireless device 2612, or computing device 2614 may also act as a server to deliver or save content to any number of other client devices, systems, equipment, streaming configurations, or databases.

In another embodiment, a cable or wire may be utilized to communicate the video directly to the wireless device 2612, computing device 2614, or to an external transceiver that is not integrated with the case 2601 of the portable endoscope 2600. The same cable may also be utilized to power (or charge) the portable endoscope 2600 from a remote location further reducing the required size of the portable endoscope 2600. For example, a USB cable (e.g. standard, mini, micro, etc.) connected to a USB port of the portable endoscope 2600 and the wireless device 2612 may be utilized to both power the portable endoscope 2600 and view video from the portable endoscope 2600. The connector may be integrated with the case 2601 or transceiver 2606 and may allow the portable endoscope 2600 to be easily utilized in a wired or wireless configuration. For example, the portable endoscope 2600 may be utilized as a plug-and-play device with any number of computing or communications devices for utilization by medical professionals, dentists, electricians, and any number of users.

A second end 2605 of the case 2601 may be removable for inserting or removing the components of the portable endoscope 2600. For example, the second end 2605 of the case 2601 may snap in, interconnect, latch, or include threads for securing the components of the case 2601. The portable endoscope 2600 may communicate with the wireless device 2612 or the computing device 2614. The portable endoscope 2600 may similarly be snapped into, attached to, inserted within, or integrated with the endoscopic sheath 2620 during utilization.

In one embodiment, the components of the portable endoscope 2600 may be interchangeable. For example, even the relative positioning of components, such as the transceiver 2606 and battery 2608 may be varied. For example, the transceiver 2606 may more efficiently transmit and receive signals when positioned at the second end 2605 of the portable endoscope 2600 where the battery 2608 is shown. As a result, the portable endoscope 2600 may be configured for each patient or medical professional. For example, different cameras or batteries may be inserted into the case 2601 for different situations, in one embodiment, the camera 2602, which may include a video camera, may be an infrared camera or spectrum-specific camera configured to view blood flow (or the lack thereof) within the nose. For example, the internal components of the portable endoscope 2600 may be changed to a new sterile case each time the portable endoscope 2600 is used to save costs and prevent waste.

In another embodiment, the components of the portable endoscope 2600 are permanently connected together. In one example, the portable endoscope 2600 may be disposable or recycled or refurbished after a single use.

In one embodiment, the components of the portable endoscope 2600 are powered by die battery 2608. The battery 2608 may be an energy dense storage device. For example, the battery 2608 may be a rechargeable or one-time use polymer battery, alkaline, zinc-air battery, lithium ion battery, thin film battery, ultra capacitor, fuel cell, piezo electric generator, or other next generation capacitors or batteries. The portable endoscope 2600 may be utilized repeatedly by replacing the battery 2608 as needed. In embodiments where the endoscopic sheath 2620 includes electrical components, the endoscopic sheath may also be powered by the battery 2608. As described, the portable endoscope 2600 or the endoscopic sheath 2620 may also be powered by the wireless device 2612 or the computing device 2614.

In another embodiment, the portable endoscope 2600 may include a port or interface mot shown) for recharging the battery 2608 without removing the battery 2608 from the case 2601. Similarly, the portable endoscope 2600 may be configured to function in a wireless or wired state. For example, the portable endoscope 2600 may be connected directly to the computing device 2614 utilizing a cable, bus, wire, or connector, such as a micro-USB to USB connector for receiving power and communicating video content. Additionally, the portable endoscope 2600 may not include the battery 2608 and instead may be powered and display video content through the wireless device 2612 or computing device 2614. For example, if the medical professional utilizes the wireless features of the portable endoscope draining the battery 2608, the portable endoscope 2600 may be connected to the computing device 2614 for the additional power requirements while simultaneously charging the battery 2608 for subsequent wireless usage. In another embodiment, the portable endoscope 2600 may be capable of being directly charged by a wall outlet or other stationary or semi-stationary form of power supply or utilizing a wireless charging station, such as an inductive charger integrated with the portable endoscope 2600.

In one embodiment, the camera 2602, light 2604, transceiver 2606, and battery 2608 may be interconnected by magnetic contacts, leads, pins, or connectors (not shown). The magnetic contacts automatically align and attach the components when placed in proximity to one another. As a result, a medical professional or other individual may easily add, exchange, or remove the various electrical components of the portable endoscope and know that the components will self-attach when placed in proximity to one another. The magnetic leads may include contacts for power, logic, or command signals, as well as video communications between each component.

In another embodiment, leads, wires, traces, contacts, or connectors may be integrated with or built into the case 2601 for communicating power, video, control signals, or other signals between the camera 2602, transceiver 2606, and battery 2608 which may also include contacts or leads for interfacing with the case 2601. The communications components of the case 2601 may allow the components to be reconfigured while maintaining functionality. Ridges or other guides may be specific to each component and may align each component with the communications and power mediums for ensuring a proper electrical connection and that power, communications, and control signals are properly communicated between the components of the portable endoscope 2600. The case 2601 may also include insulators that prevent bleed over, noise, and cross-talk to keep the distinct signals separate for each portion of the trace. In one embodiment, the case 2601 may be the walls 2622 of the endoscopic sheath 2620 and the electrical components of the portable endoscope 2600 may be encased within the walls 2622 of the endoscopic sheath 2620.

In another embodiment, the camera 2602, transceiver 2606, and battery 2608, and other described components may communicate signals utilizing ports, contacts, adapters, or male and female connectors. For example, the connectors may be pin, sleeve, and socket connectors of a reduced size, such as a version of a mini-DIN, S-video, DVI, USB, coaxial, or HDMI connectors (micro video connectors). However, any other form of standard or proprietary connectors may be utilized to connect the electrical components of the portable endoscope.

In one embodiment, the connectors may have a footprint of 0.25 mm-1 cm (diameter, area, length, etc); however, larger and smaller footprints are also possible. In addition, the diameter of the endoscopic sheath 2620 and portable endoscope 2600 may vary between approximately 0.1 mm and 1.5 cm with other sizes being produced for different applications. For example, the portable endoscope 2600 may be small enough to fit into an artery or vein. The portable endoscope 2600 or endoscopic sheath 2620 may vary in size from pencil or straw sized to coffee straw or needle sized based on the type of manufacturing and design processes utilized for the portable endoscope 2600.

In one embodiment, the camera 2602 is cylindrically shaped and is inserted or partially encased in the light 2604. The light 2604 may also be doughnut, or annular shaped and configured to receive the camera 2602 in a center portion or hole. During assembly of the various parts, the light 2604 and camera 2602 may be changed out as has previously been described. However, the camera 2602 and the light 2604 may be semi-circularly shaped.

The components of the portable endoscope 2600 or endoscopic sheath 2620 may include longitudinal or lateral ridges, notches, or other alignment structures for properly aligning a component, such as the light 2604 and camera 2602 with the transceiver 2606 and battery 2608. For example, a ridge (not shown) along the top of the cylindrically-shaped camera 2602 may prevent the camera 2602 from being inserted in the light 2604 except when in the proper alignment. Similar ridges may be included on the light 2604, transceiver 2606, battery 2608, and logic if present. A corresponding notch on the case 2601 may align the components.

In another embodiment, portions or components of the portable endoscope 2600 may be separated by flexible connectors (not shown) (e.g., centipede configuration) that allow distinct components or portions of the portable endoscope 2600 to be individually angled and positioned. For example, wired connectors between each component of the portable endoscope 2600, such as a bus configured to communicate video signals and power, may enhance flexibility. For example, the light 2604 and camera 2602 portion of the portable endoscope 2600 may be angled, bent, or positioned a particular direction, relative to the remainder of the portable endoscope 2600, before insertion into the nose to view a selected sinus. The separated flexible portions of the portable endoscope 2600 or endoscopic sheath 2620 may be manually adjusted or controlled by one or more servos or drive mechanisms. In one example, a mechanical pivot that provides resistive adjustments may be twisted to achieve the desired configuration of the portable endoscope 2600. For example, a graphical user interface accessible through the computing device 2614 may be utilized to receive user selections or commands to pivot or rotate the portion of the portable endoscope 2600 or the endoscopic sheath 2620 including the camera 2602 and light 2604.

The electrical components of the portable endoscope 2600 may be manufactured utilizing processes for plastic, organic, and inorganic semiconductors, substrates, electronics, and logic. For example, the light 2604, transceiver 2606, and battery 2608 may include flexible plastic-based substrates that function with printable conductive inks, organic light-emitting diode (OLED) layers and materials, or active-matrix thin-film-transistor arrays. Multilayer composite structures may be utilized to create and manufacture the portable endoscope 2600. For example, roll-to-roll processing with inkjet printing or spray deposition may be utilized to produce the flexible and reduced footprint components of the portable endoscope 2600. In one embodiment, the entire portable endoscope 2600 may be configured to flex to be moved and positioned to the correct location. Magnetic coupling, wires, and MEMs connections may be utilized to bend and flex the portable endoscope 2600.

The computing device 2614 or the wireless device 2612 may include a wireless adapter 2607. The wireless adapter 2607 is a transceiver configured to send and receive a signal to and from the portable endoscope 2600. The wireless adapter 2607 may be utilized with any number of electronic devices to receive or format the video content in real-time. In one embodiment, the wireless adapter 2607 is an adapter, such as a USB adapter, dongle, or other wireless interface configured to receive wireless communications from the portable endoscope 2600, and may decode, decrypt, or format the video signal retrieved by the camera of the endoscope 1202 for view by a medical professional or other party. The wireless adapter 2607 may utilize any of the standards that are previously described to communicate with the portable endoscope 2600. The wireless adapter 2607 may be internally integrated with the computing device 2614 (e.g., Bluetooth, near field communications, WiFi, etc.) or may be externally connected.

In another embodiment, the camera 2602 and light 2604 may both be stacked or placed side by side. In another embodiment, the camera 2602 or light 2604 may utilize different shapes, such as an ellipse, semi-circle, square, rectangle, or oval.

As previously noted, the portable endoscope 2600 may be configured to bend with the motion of the scope port and working ports. The controls of the endoscopic sheath 2620 may control the position, motion, or operation of the endoscopic sheath 2620. For example, the controls of the endoscopic sheath 2620 (e.g. dial or trigger) may control the position or motion of the endoscopic sheath 2620 including the working ports and scope ports (including the portable endoscope 2600) as are herein described. In other embodiments, the portable endoscope 2600 and the endoscopic sheath 2620 may include a physical or wireless connection for powering on/off the portable endoscope 2600, turning the camera 2602 or light 2604 on or off, adjusting intensity or wavelength of the light 2604, managing resolution, sensitivity, or format of the content captured by the camera 2602, and otherwise managing the portable endoscope 2600. The portable endoscope 2600 may be inserted within the endoscopic sheath 2620 or built-in.

FIGS. 27 and 28 are schematic front views of the portable endoscope 2600 in accordance with illustrative embodiments. FIG. 27 illustrates the portable endoscope 2600 having an oval shape. The light 2604 may be formed from arc or boomerang-shaped lights. The light 2604 may emit a single spectrum of light or distinct spectra depending on the requirements of the medical professional or medical condition. For example, an upper portion 2606 of the light may be a miniaturized halogen light configured to emit a bright white light and the lower portion 2608 of the light may be an infrared LED that may be activated as needed. In one embodiment, the light 2604 and camera 2602 may directly abut each other. In another embodiment, any number of spacers or separators may be built into the case 2601, camera 2602, or light 2604 to correctly position the various components.

Turning again to FIG. 26, the light 2604 may be a single light or may be composed of multiple lights that transmit light or signals at different frequencies or intensities. For example, different lights may be turned on at different times and intensity to examine cartilage, bone, blood flow, skin, or other forms of tissue. In one embodiment, the camera 2602 may fixedly or movably extend or protrude from the end of the portable endoscope 2600 to provide an uninhibited view of portions of die body during use.

In one embodiment, the camera 2602 may be connected to a motor that allows the camera 2602 to extend a small distance from the end of the portable endoscope 2600 or endoscopic sheath, rotate, or pivot. For example, the case 2601 may include bearings or rollers (not shown) for extending and rotating the camera 2602. The motor may be controlled remotely utilizing logic included in the portable endoscope 2600. For example, the wireless device 2612 may include a graphical user interface for rotating or pivoting the camera 2602, extending the camera 2602, switching between light spectrums, and recording video content. The portable endoscope 2600 may also include one or more buttons or switches for turning the portable endoscope on/off, adjusting intensity/brightness, or controlling the other functions of the portable endoscope 2600. The portable endoscope 2600 including the switch (not shown) may also include controls for these functions as well, in addition, the camera 2602 may be able to zoom in and out. In one embodiment, the camera 2602 may utilize a fly eye configuration to get multiple views.

In another embodiment, portions of the portable endoscope 2600, such as the camera 2602 and light 2604, may be externally connected to the transceiver 2606 and battery 2608 by a cable (not shown). As a result, the size of the portable endoscope 2600 may be reduced even further. For example, the cable of the portable endoscope 2600 may be incorporated into an elastic, Velcro band, or securing component of a nasal guide. The cable may include a video cable for communicating a video signal to the transceiver 2606 as well as a wire for providing power from the battery 2608. In one embodiment, the transceiver 2606 and the battery 2608 may be attached or integrated into the securing component of the nasal guide or into a handle of the endoscopic sheath 2620. For example, the transceiver 2606 and an integrated antenna may be built into the handle of the endoscopic sheath 2620 as well as die battery 2608. The battery 2608 may be disposable or a rechargeable 9V battery that is easily inserted into the handle for powering the portable endoscope 2600 and endoscopic sheath 2620. In another example, a Velcro band for securing the nasal guide may include a pocket for inserting the transceiver 2606 and battery 2608, and the cable may be similarly integrated. In one embodiment, the transceiver 2606 may also include a port (not shown) for connecting the portable endoscope 2600 to the wireless device 2612 or computing device 2614 to view the video content and perform the medical procedure with the visual assistance of the portable endoscope 2600.

The first end 2603 of the portable endoscope 2600 may have a diagonal concave shape for preventing blood, mucous, pus, or other fluids from accumulating on the first end 2603 thereby blocking the view of the camera 2602 and the output of the light 2604. Blood or other fluids that accumulates on the first end 2603 preferably runs to the bottom or side of the portable endoscope 2600 because of the shape.

In another embodiment, the first end 2603 may be rounded with an even concave or convex shape that pushes or maintains an air bubble in front of the first end 2603 of the portable endoscope 2600 during utilization keeping the camera 2602 unobstructed.

Figure 29:
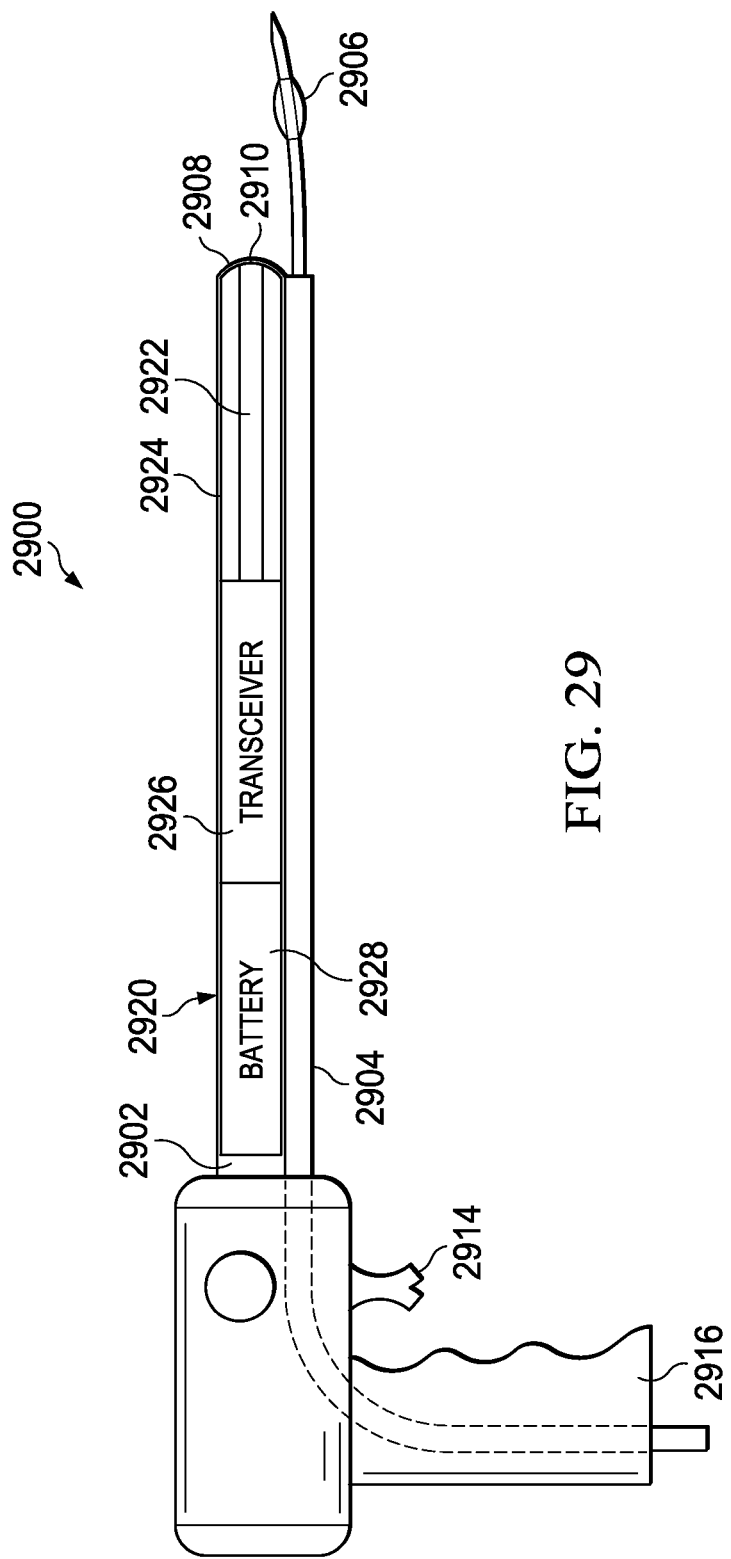
FIG. 29 is a schematic, pictorial representation of an endoscopic sheath in accordance with another illustrative embodiment.

FIG. 29 is a schematic, plan view of an endoscopic sheath 2900 in accordance with another illustrative embodiment. In one embodiment, the endoscopic sheath 2900 includes a scope port 2902, a working port 2904, a balloon catheter 2906, a lens 2908, a first end 2910, a second end 2912, a balloon control 2914, and a handle 2916.

The endoscopic sheath 2900 may also include a portable endoscope 2920 including a camera 2922, a light 2924, a transceiver 2926, and a battery 2928. The portable endoscope 2920 may be inserted in the scope port 2902 or may be integrated as a permanent portion of the endoscopic sheath. The portable endoscope 2920 is described in greater detail in FIG. 26.

Figure 30:
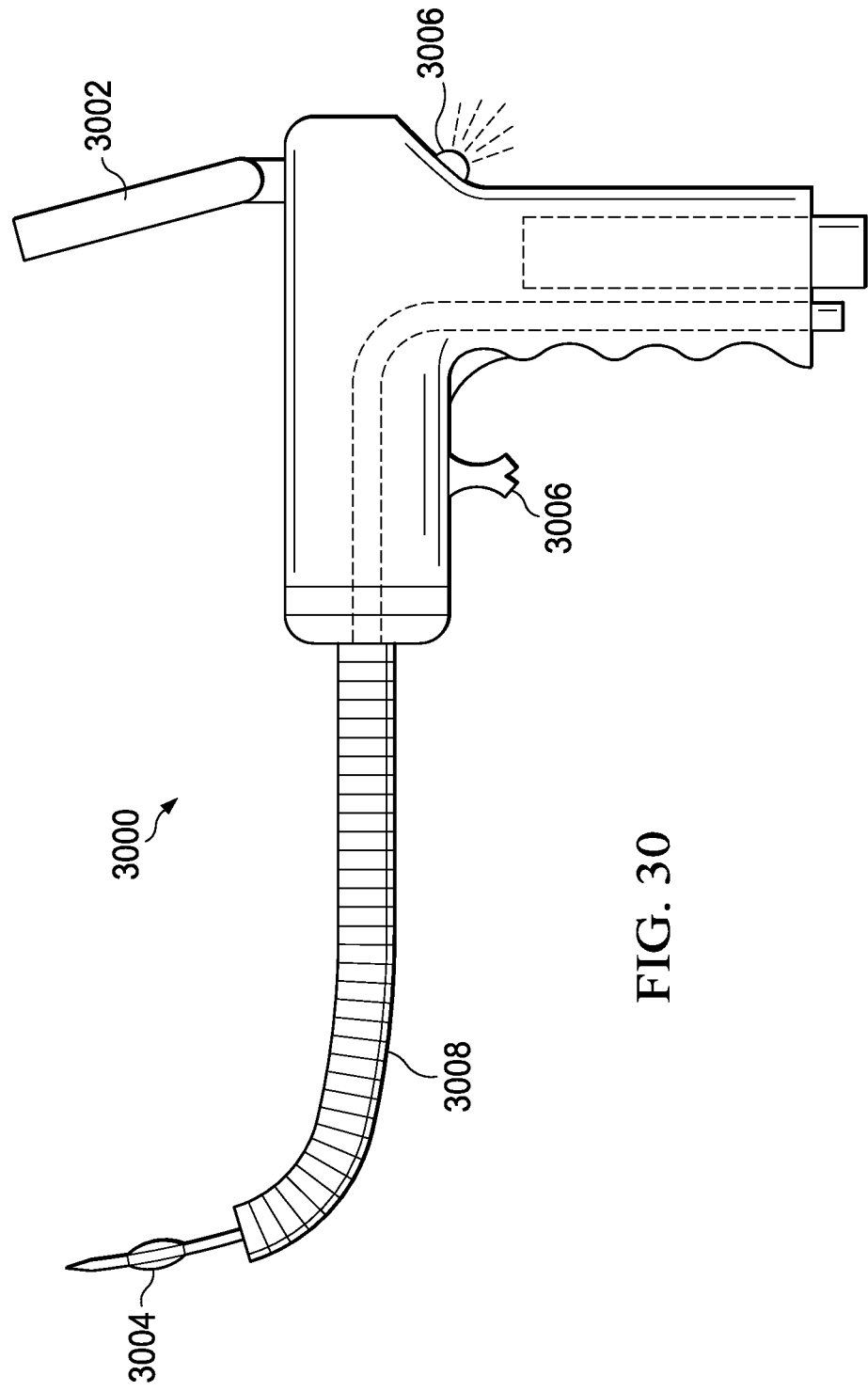
FIG. 30 is a schematic, plan view of an endoscopic sheath in accordance with another illustrative embodiment.

FIG. 30 is a schematic, plan view of an endoscopic sheath 3000 in accordance with another illustrative embodiment. The endoscopic sheath 3000 may include any number of the components and features as are previously described. In addition, the endoscopic sheath 3000 may include a display 3002. The display 3002 may allow a medical professional to control movement and operation of the endoscopic sheath 3000 and a balloon catheter 3004 utilizing any of the included controls.

The display 3002 may be positioned or angled so that the view of the medical professional is not diverted away from the patient. Instead, the medical professional may look at the insertion point and patient and the view of the endoscopic sheath 3000 simultaneously. Video may transmitted to the display 3002 by a fiber optic camera within the balloon catheter 3004 or by a portable endoscope (not shown) attached the endoscopic sheath 3000. In one embodiment, the display 3002 is removable and may be located and positioned as needed by the medical professional. The display 3002 may include a stand-alone battery and transmitter for communicating with the endoscope or other video components. For example, the endoscopic sheath 3000 may include an electrical interface (e.g. SCSI, USB, etc) for clocking with the display 3002. In one embodiment, the display 3002 may include Velcro, a hanger, or other securing mechanism or component for positioning the display 3002.

In one embodiment, the display 3002 may be a wireless device or tablet device that may be attached to the endoscopic sheath 3000. For example, the endoscopic sheath 3000 may include a docking station or connector for wired or wireless connection with the wireless device acting as the display 3002.

The endoscopic sheath 3000 may include directional controls 3006. The directional controls 3006 may be utilized to position a guide 3008 encompassing one or more lumens. The directional controls 3006 may include controls for controlling the directional guide, advancing and retracting the balloon catheter 3004, and inflating and deflating the balloon catheter 3004.

In any of the previous Figures and described embodiments, the balloon catheter or endoscopic sheath may utilize controllable guide wires as is known in the art and include lumens and ports for applying either or both suction and irrigation as needed.

Figure 31:
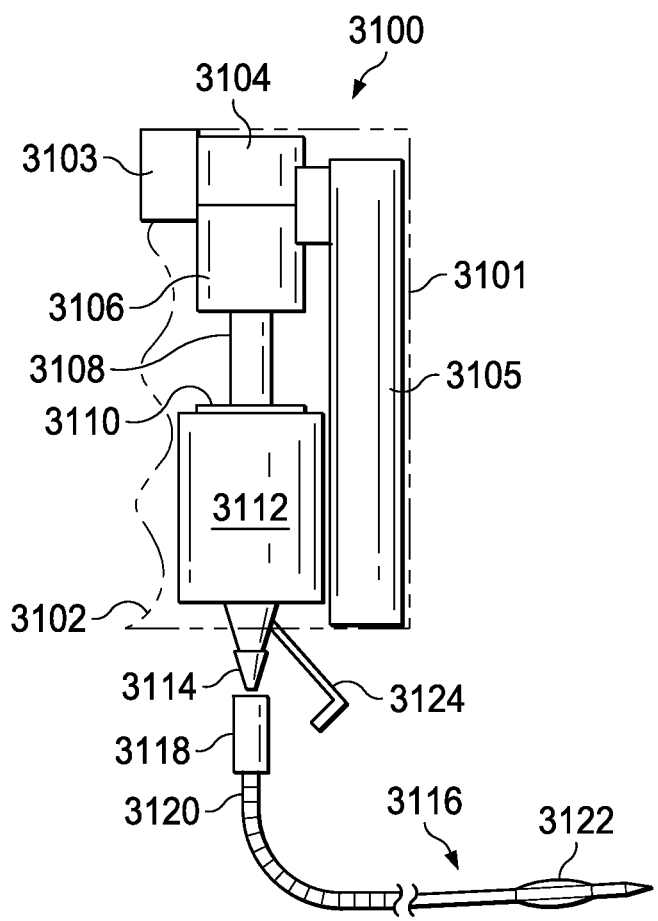
FIG. 31 is a cut-away view of an inflation handle in accordance with an illustrative embodiment.

FIG. 31 is a cut-away view of an inflation handle 3100 in accordance with an illustrative embodiment. In one embodiment, the inflation handle 3100 includes a housing 3101, a grip 3102, a trigger 3103, logic 3104, a battery 3103, a pump 3106, a piston 3108, a plate 3110, an inflation cartridge 3112, a nozzle 3114, a balloon catheter 3116, a sleeve 3118, a notched section 3120, a balloon 3122, and a catch 3124.

The housing 3101 is the encasing framework of the inflation handle 3100. In one embodiment, the housing 3101 may be formed of plastic, rubber, polymers, metal, composite or other materials. The housing 3101 may include smooth or non-slip surfaces that allow the medical professional to better grip, hold, or secure the inflation handle 3100 during utilization.

The trigger 3103 is the selection element for activating and deactivating the pump 3106. In one embodiment, the trigger 3103 is a button that may be selected or deselected to activate and deactivate the pump, respectively. In another embodiment, the trigger 3103 may include multiple components that allow the medical professional to actively select to activate the pump 3106 or deactivate the pump 3106. As a result, the pressure in the balloon catheter 3116 may be maintained until released. In one embodiment, the trigger 3103 is connected to the logic 3104 for activating the pump 3106 utilizing an electronic signal. For example, the trigger 3103 may include a switch for activating the pump 3106. In another embodiment, the battery 3105 is not needed, and instead the trigger 3104 is a mechanical component that drives the motion of the pump 3106 and piston 3108. For example, each time the trigger 3103 is pressed, the pump 3106 may drive the piston 3108 a designated amount. As a result, the medical professional may quickly inflate and deflate the balloon 3122 with or without the use of the battery 3105.

In another embodiment, the inflation handle 3100 may include a display that displays information, such as status of the battery, pressure of the balloon catheter 3116, and maximum pressure set for the inflation handle 3100. The inflation handle 3100 may include a dial, readout, buttons, or other controls for setting the pressure utilized to inflate the balloon catheter 3116. For example, once the maximum pressure is reached, the pump 3106 may hold the pressure steady.

The logic 3104 is the electronic controls for the inflation handle. The logic 3104 may include any combination of a processor, memory, application-specific integrated circuit, (ASIC), IC, field-programmable gate array (FPGA), programmable EEPROM, system-on-chip, or other digital logic or process for executing a software application or operating system. In one embodiment, the logic 3104 may include one or more sensors for sensing or determining the pressure applied to inflate the balloon 3122 by the inflation cartridge 3112. For example, the logic 3104 may measure the pressure output through the nozzle 3114. In another embodiment, the pressure applied by the piston 3108 may be utilized to determine the pressure in the balloon 3122. Any number of tables, databases, or test data may be stored in the logic for utilizing the characteristics and settings of the inflation handle 3100 and balloon catheter 3116 (e.g., length, diameter, balloon size, etc.) to determine the maximum pressure and the applied pressure.

In one embodiment, the pump 3106 drives motion of the piston 3108 to expel and suction fluid from and into the inflation cartridge 3112. The pump 3106 may be or include an actuator driving the piston 3108. In another embodiment, the pump 3106 may be a miniature or micro fluid pump as is known in the art. For example, the piston 3108 may instead be a conduit, tube, or other communications medium for pumping fluid into or out of the inflation cartridge 3112. In one embodiment, the pump 3106 may pump a gas, such as air, into the inflation cartridge 3112 to push fluid from the nozzle 3116 of the inflation cartridge 3112 into the balloon catheter 3116.

The position of the inflation cartridge 3112 vertically within the inflation handle 3100 may allow a gas or less dense fluid to be pumped into the inflation cartridge 3112 and remain at a top portion of the inflation cartridge 3112 without being communicated into the balloon catheter 3116. In another embodiment, one or more filters, baffles, or fluid stops may prevent either fluid from entering the pump 3106 or gas from entering the balloon catheter 3116. The filters may be utilized to ensure that the pump never touches a fluid that may contaminate the inflation handle 3100 and instead all of the portions of the inflation handle that are exposed to fluid, such as the inflation cartridge 3112 and the balloon catheter 3116 are disposed of during each use, while the inflation handle 3100 may be reused repeatedly. For example, the inflation cartridge 3112 may include ports, nozzles, or openings for applying pressure and suction to the inflation cartridge 3112.

The pump 3106, piston 3108, inflation cartridge 3112, or other component of the inflation handle 3100 may include one or more sensors for determining the pressure/resistance applied by the piston 3108 or pump 3106 or the pressure within the inflation cartridge 3112 or balloon catheter 3116. Information from repeated usage, clinical trials, or historical results may be utilized to ensure that the pressure applied to the inflation cartridge 3112 results in the proper pressure or pressure range at the balloon 3122. In one embodiment, the inflation cartridge 3112 may include markings indicating the pressure applied or displacement of the piston 3108. The markings may correspond to a window in die housing 3101 that allows the medical professional to determine the pressure being applied. For example, the position of the plunger that is attached to the piston 3108 or the fluid level in the inflation cartridge 3112 may indicate either the pressure applied in the inflation cartridge 3112 or the pressure applied at the balloon 3122.

In one embodiment, the housing 3101 may include cut-aways, hinges, compartments, etc. for receiving the inflation cartridge 3112 or the battery 3105. For example, the inflation handle 3100 may be hinged or have a clam configuration for opening the housing 3101 to insert the inflation cartridge 3112 or replace the battery 3105. The battery 3105 may power or communicate with the logic 3104 to perform the various functions and processes herein described. The battery 3105 may be a battery pack or a single battery (e.g. AAA or AA battery) as is herein described.

The inflation handle 3100 may also include a port for powering the inflation handle 3100 or charging the battery 3105 as is known in the art. An indicator or display of the inflation handle 3100 may indicate the charge level of the battery 3105 or how many more inflation and deflation operations may be performed before the battery 3105 is exhausted. In one embodiment, the logic 3104 may include a miniature speaker or vibrator (not shown) that plays an alert or vibrates when the balloon 3122 has reached a designated pressure or when the balloon 3122 has been maintained at the designated pressure for a pre-determined amount of time. The logic 3104 may further include a display that indicates the pressure applied, LEDs for indicating whether the inflation has been successfully implemented (green—inflation complete successful, red—inflation not completed, yellow—inflation handle 3100 error).

The nozzle 3114 expels the fluid from the inflation cartridge 3112. In one embodiment, the nozzle 3114 is conically shaped. For example, the narrowing shape of the nozzle 3114 may be utilized to puncture, pierce, rupture, or break a seal of a balloon catheter 3116 that is pre-filled with saline and sealed at an end of the sleeve 3118. The nozzle 3114 may also include barbs, threads, ridges (parallel or perpendicular) for receiving the sleeve of the balloon catheter 3118. In one embodiment, the nozzle 3114 and sleeve 3118 may include threads for being secured or screwed together. The catch 3124 may be further utilized to secure the sleeve 3118 against the nozzle 3114. In one embodiment, the catch 3124 may be a hinged or flexing arm with a collar that partially surrounds the notched section 3120 (or smooth surface of the balloon catheter). The catch 3124 may abut against the other side of the sleeve 3118 preventing the sleeve 3118 from slipping off the nozzle 3114 when the inflation pressure is applied.

The notched section 3120 of the balloon catheter 3116 may be utilized for applications where the balloon catheter 3116 is moved. For example, the notched section 3120 may include miniature grooves (e.g., around the full diameter of the balloon catheter 3116, or on one or more sides or portions) for driving the balloon catheter 3116. For example, the balloon catheter 3116 may be utilized with embodiments of the endoscopic sheath to move the balloon catheter 3116 in and out of the endoscopic sheath. For example, a ratcheting/pawl mechanism, gears, or other mechanical components may grip or secure the indentations of the notched section 3120 to advance and retract the balloon catheter 3116. For example, the inflation handle 3100 or endoscopic sheath may include controls for both controlling in which direction pawls (e.g., biased locking pawls and driving pawls as are known in the art) engage with the indentations of the notched section 3120 and driving motion of the balloon catheter 3116 (e.g., triggers, finger dials, etc.). The length of the notched section 3120 may correspond to the medical procedure. For example, the length of the notched section 3120 for balloon sinuplasty may be approximately 5" along a portion of the balloon catheter 3116 while the notched section 3120 may be 8-12" long for a laparoscopic procedure.

The notched section 3120 may also be utilized with housings, surgical instruments, catheters, and other medical instruments, equipment, and accessories. In one embodiment, the notched section 3120 is sized, such that the notched section 3120 never enters the patient's body because of the possible abrasive nature of the notched section. For example, the notched section may be from 3-12" long depending on the application. In one embodiment, the notched section 3120 may not extend all the way to the sleeve 3118 and may be positioned in the middle or towards the sleeve 3118 end of the balloon catheter 3116.

In one embodiment, the inflation handle 3100 may include a clamp, receptacle, slot, enclosed door, buckle, latch, or other component for opening, accessing, and then securing the components of the inflation handle 3100. The clamp may be integrated with or attach to any side, top, or bottom of the inflation handle 3100.

Figure 32:
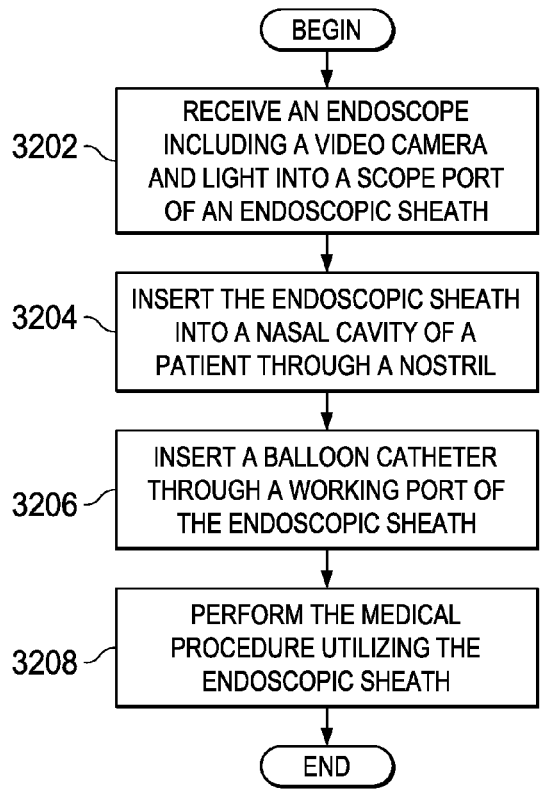
FIG. 32 is a flowchart of a process for utilizing an endoscopic sheath in accordance with an illustrative embodiment.

FIG. 32 is a flowchart of a process for utilizing an endoscopic sheath in accordance with an illustrative embodiment. The process of FIG. 32 may be performed by one or more medical professionals utilizing an endoscopic sheath and an endoscope. The endoscope may be a standard wired endoscope or a portable endoscope as herein described.

The process may begin by receiving an endoscope including a video camera and a light into a scope port of the endoscopic sheath (step 3202). The endoscope may be a wired endoscope, portable endoscope, or borescope to reduce the cost. The endoscopic sheath may include one or more lumens or ports.

Next, the endoscopic sheath is inserted into a nasal cavity of a patient through a nostril (step 3204). The endoscopic sheath may be utilized for both nostrils or a separate endoscopic sheath may be utilized for each nostril. In one embodiment, the endoscopic sheath is cleansed, swashed, or rinsed in an antibacterial solution before or after use. In another embodiment, the endoscopic sheath may be received into any orifice, body part, or natural or surgically created opening.

Next, a balloon catheter is inserted through a working port of the sheath (step 3206). The balloon catheter may be inserted into the working port before or after the endoscopic sheath is inserted into the patient. The balloon catheter may alternatively be any number of medical instruments, accessories, or so forth.

Next, the medical procedure is performed utilizing the endoscopic sheath (step 3208). The endoscopic sheath may also be utilized to control (e.g., advance, retract, rotate, position, angle, etc.) the balloon catheter or instrument. For example, the endoscopic sheath may be utilized to inflate the balloon of the balloon catheter. The endoscopic sheath may also be utilized to irrigate, suction, or further examine a portion of the patient's body.

Figure 33:
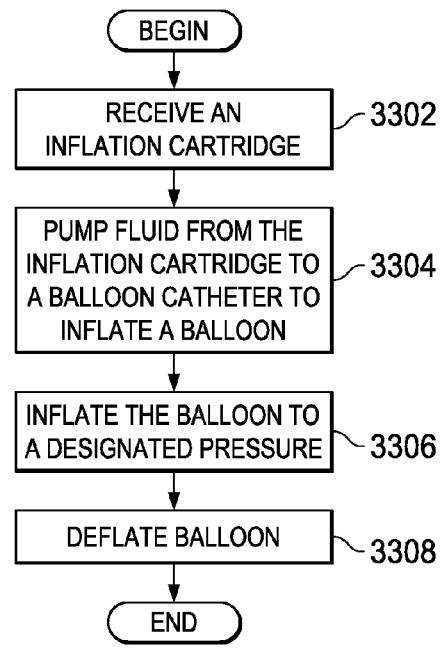
FIG. 33 is a flowchart of a process for inflating a balloon in accordance with an illustrative embodiment.

FIG. 33 is a flowchart of a process for inflating a balloon in accordance with an illustrative embodiment. The process of FIG. 33 may be implemented by an endoscopic sheath, inflation handle, system, or other device that inflates a balloon, or device that performs irrigation or suction in accordance with illustrative embodiments. In one embodiment, the system may be configured to receive an inflation cartridge. For example, the inflation cartridge may be disposable and filled with saline.

The inflation cartridge may be configured to connect directly to a balloon catheter to prevent unnecessary contamination or contact with other portions of the system. As a result, both the balloon catheter and inflation cartridge may be disposed for ease of use. In one embodiment, the inflation cartridge may include a nozzle that may be configured to receive a sleeved end of the balloon catheter. A hinged clamp, overlay, or other connector may connect the nozzle to an end of the balloon catheter.

The process of FIG. 33 may begin with the system receiving an inflation cartridge 3302. In one embodiment, the inflation cartridge may include female connectors for connecting to male connectors of the system. For example, the saline cartridge may include tabbed recesses for receiving tabbed connectors of the system (e.g., L-shaped recesses and connectors that lock into place). The inflation cartridge may be utilized to inflate the balloon, irrigate a portion of the body, or provide suction.

Next, the system pumps fluid from die inflation cartridge to a balloon catheter to inflate a balloon (step 3304). In one embodiment, a piston, or screw drive attached to the connector may drive a portion of the saline cartridge to expel the fluid from the cartridge into the balloon catheter. The fluid may be a liquid or gas. In one embodiment, the balloon catheter may include choke points for preventing gas from reaching the balloon if gas is utilized to inflate the balloon. In another embodiment, a miniature or micro pump as is known in the art may pump the fluid in the inflation cartridge into the balloon catheter.

The system inflates the balloon to a designated pressure (step 3306). The system may utilize known conditions, such as the fluid, length of the balloon catheter, type of balloon, and other conditions to apply the proper pressure. The designated pressure may be determined by the motion or operation of the pump or utilizing one or more sensors integrated within the system or balloon catheter. For example, the extension of the piston or rotations of the screw drive may indicate the pressure applied at the balloon. The system may also include logic, instructions, or algorithms to ensure that the designated pressure is met, but not exceeded.

Next, the system deflates the balloon (step 3308). The balloon may be deflated by allowing the pressure to gradually decrease or by actively utilizing the inflation cartridge or pump. For example, by moving the cartridge, suction may be created drawing the fluid back out of the balloon catheter.

The previous detailed description is of a small number of embodiments for implementing the invention and is not intended to be limiting in scope. The following claims set forth a number of the embodiments of the invention disclosed with greater particularity.

What is claimed:

1. An endoscopic sheath, comprising:
   a sheath body having an operating end and a handling end wherein the handling end comprises a grasping portion having a housing with one or more port controls and an inflation port operably configured for inflating balloon catheters;
   a scope channel within the sheath body having a scope channel opening at the handling end configured to receive an endoscope and the scope channel having an optical lens in covering relation over the scope channel at the operating end;
   a working channel extending through the housing of the grasping portion and terminating at the operating end of the sheath body, wherein the working channel has a working channel opening at the operating end of the sheath body, and the working channel is indirectly connected to the inflation port on the housing of the grasping portion at the handling end of the sheath body;

a port wall between and separating the scope channel and working channel, wherein the scope channel and working channel are vertically aligned;

a bending section comprising a portion of the scope channel and a portion of the working channel;

a directional control disposed on the housing of the grasping portion, the directional control electrically connected with one or more actuators within the housing, the one or more actuators configured to actuate articulation of the bending section;

a balloon catheter comprising an insertion end with a balloon and an opposite connection end operably connected to the housing of the grasping portion at the inflation port, wherein a portion of the balloon catheter is housed within the housing of the grasping portion and within the working channel, wherein the balloon catheter is advanced from the housing of the grasping portion towards the operating end of the sheath body through the working channel by at least one of the one or more port controls; and a balloon catheter control disposed on the housing of the grasping portion of the sheath body, the balloon catheter control operably configured to control one or more balloon catheter operations;

wherein the scope channel and working channel are arranged parallel within the sheath body, both the scope channel, the working channel and the port wall having terminal ends terminating at the operating end of the sheath body opposite the grasping portion.

2. The endoscopic sheath according to claim 1, wherein the endoscope is a wireless endoscope.

3. The endoscopic sheath according to claim 1, wherein the one or more port controls comprise an advancer for advancing and retracting the balloon catheter.

4. The endoscopic sheath according to claim 3, wherein the one or more port controls comprise an inflation control on the housing of the grasping portion, the inflation control operably connected to the inflation port and the balloon catheter for inflating a balloon of the balloon catheter.

5. The endoscopic sheath according to claim 4, wherein the inflation control includes a manual trigger for inflating the balloon.

6. The endoscopic sheath according to claim 4, wherein the inflation control includes an electronic pump for inflating the balloon to a pre-defined pressure.

7. The endoscopic sheath according to claim 4, wherein the inflation control comprises an inflation pressure setting for setting the balloon to a pre-defined pressure.

8. The endoscopic sheath according to claim 1 wherein:

the directional control receives a manual user input, produces a control signal, and sends the control signal to one or more electromechanical components of the bending section to move to bending section in multiple direction and/or planes, wherein the bending section further comprises hinge elements for controlling a bending motion of the portions of the scope port and the working port.

* * * * *